United States Patent
Yamamoto et al.

(10) Patent No.: US 10,939,804 B2
(45) Date of Patent: Mar. 9, 2021

(54) ENHANCED FLEXIBLE ROBOTIC ENDOSCOPY APPARATUS

(71) Applicant: ENDOMASTER PTE LTD, Singapore (SG)

(72) Inventors: Tomonori Yamamoto, Singapore (SG); Isaac David Penny, Singapore (SG); Christopher Lee Shih Hao Sam Soon, Singapore (SG); Hoang-Ha Tran, Singapore (SG); Tae Zar Lwin, Singapore (SG); Tsun En Tan, Singapore (SG); Naoyuki Naito, Tokyo (JP); Takahiro Kobayashi, Tokyo (JP); Makio Oishi, Tokyo (JP)

(73) Assignee: ENDOMASTER PTE LTD, Singapore (SG)

( * ) Notice: Subject to any disclaimer, the term of this patent is extended or adjusted under 35 U.S.C. 154(b) by 0 days.

(21) Appl. No.: 15/127,398

(22) PCT Filed: Mar. 19, 2015

(86) PCT No.: PCT/SG2015/050042
§ 371 (c)(1),
(2) Date: Sep. 19, 2016

(87) PCT Pub. No.: WO2016/148642
PCT Pub. Date: Sep. 22, 2016

(65) Prior Publication Data
US 2017/0332882 A1 Nov. 23, 2017

(51) Int. Cl.
*A61B 1/00* (2006.01)
*A61B 1/005* (2006.01)
(Continued)

(52) U.S. Cl.
CPC .......... *A61B 1/00105* (2013.01); *A61B 1/005* (2013.01); *A61B 1/0016* (2013.01);
(Continued)

(58) Field of Classification Search
CPC . A61B 1/00133; A61B 1/0057; A61B 1/0016; A61B 1/0125; A61B 1/0052;
(Continued)

(56) References Cited

U.S. PATENT DOCUMENTS 6,419,626 B1 * 7/2002 Yoon ................. A61B 1/00052
600/103
2005/0272975 A1 * 12/2005 McWeeney .......... A61B 1/0125
600/113
(Continued)

FOREIGN PATENT DOCUMENTS

EP 1 818 005 A1 8/2007
JP 2008-200494 A 9/2008
(Continued)

OTHER PUBLICATIONS

European Office Action dated May 22, 2017 for corresponding European application No. 15 807 587.9.
(Continued)

*Primary Examiner* — Aaron B Fairchild
(74) *Attorney, Agent, or Firm* — Intellectual Property Law Group LLP

(57) ABSTRACT

An enhanced flexible robotic endoscopy apparatus includes a main body and flexible elongate shaft. The main body comprises a proximal end, a distal end and a housing that extends to the proximal end and the housing comprises a plurality of surfaces and a plurality of insertion inlets which reside on at least one of the surface of the housing at the proximal end of the main body, through which a plurality of channels for endoscopy are accessible. Each of the insertion (Continued)

inlets has insertion axis corresponding thereto, along which flexible elongate assemblies are insertable, with the insertion axes of the insertion inlets being parallel to the central axis of the flexible elongate shaft at the proximal end of the flexible elongate shaft.

6 Claims, 24 Drawing Sheets

(51) Int. Cl.
    *A61B 1/012*     (2006.01)
    *A61B 34/30*     (2016.01)
    *A61B 1/04*     (2006.01)
    *A61B 1/018*     (2006.01)
    *A61B 1/06*     (2006.01)
    *A61B 17/00*     (2006.01)
    *A61B 34/37*     (2016.01)
(52) U.S. Cl.
    CPC .......... *A61B 1/0051* (2013.01); *A61B 1/0052* (2013.01); *A61B 1/0057* (2013.01); *A61B 1/00066* (2013.01); *A61B 1/00112* (2013.01); *A61B 1/00121* (2013.01); *A61B 1/00128* (2013.01); *A61B 1/00131* (2013.01); *A61B 1/00133* (2013.01); *A61B 1/00147* (2013.01); *A61B 1/00149* (2013.01); *A61B 1/012* (2013.01); *A61B 1/018* (2013.01); *A61B 1/0125* (2013.01); *A61B 1/04* (2013.01); *A61B 34/30* (2016.02); *A61B 1/00013* (2013.01); *A61B 1/00135* (2013.01); *A61B 1/06* (2013.01); *A61B 34/37* (2016.02); *A61B 2017/00477* (2013.01); *A61B 2034/301* (2016.02); *A61B 2034/302* (2016.02)
(58) Field of Classification Search
    CPC ... A61B 1/00147; A61B 1/0051; A61B 1/012; A61B 1/00149; A61B 1/00131; A61B 1/00128; A61B 1/00112; A61B 1/00121; A61B 1/00105; A61B 1/00066; A61B 1/018; A61B 1/005; A61B 1/00135; A61B 1/00087; A61B 1/00091; A61B 1/00094; A61B 17/320016; A61B 2017/00296
    USPC ........................................................ 600/146
See application file for complete search history.

(56)     References Cited

U.S. PATENT DOCUMENTS

| | | | | |
|---|---|---|---|---|
| 2006/0161045 | A1* | 7/2006 | Merril | A61B 1/018 600/117 |
| 2007/0078301 | A1* | 4/2007 | Kura | A61B 1/00133 600/106 |
| 2007/0225554 | A1* | 9/2007 | Maseda | A61B 1/018 600/104 |
| 2009/0287043 | A1* | 11/2009 | Naito | A61B 1/0052 600/104 |
| 2010/0318100 | A1* | 12/2010 | Okamoto | A61B 1/0052 606/130 |

FOREIGN PATENT DOCUMENTS

| | | |
|---|---|---|
| JP | 2015-024033 A | 2/2015 |
| WO | WO 2007/146987 A2 | 12/2007 |
| WO | WO 2010/138083 | 12/2010 |
| WO | WO 2014/133476 A1 | 9/2014 |

OTHER PUBLICATIONS

Japanese Office Action dated Jan. 7, 2019 for corresponding Japanese application No. 2018-500265 with English translation.

* cited by examiner

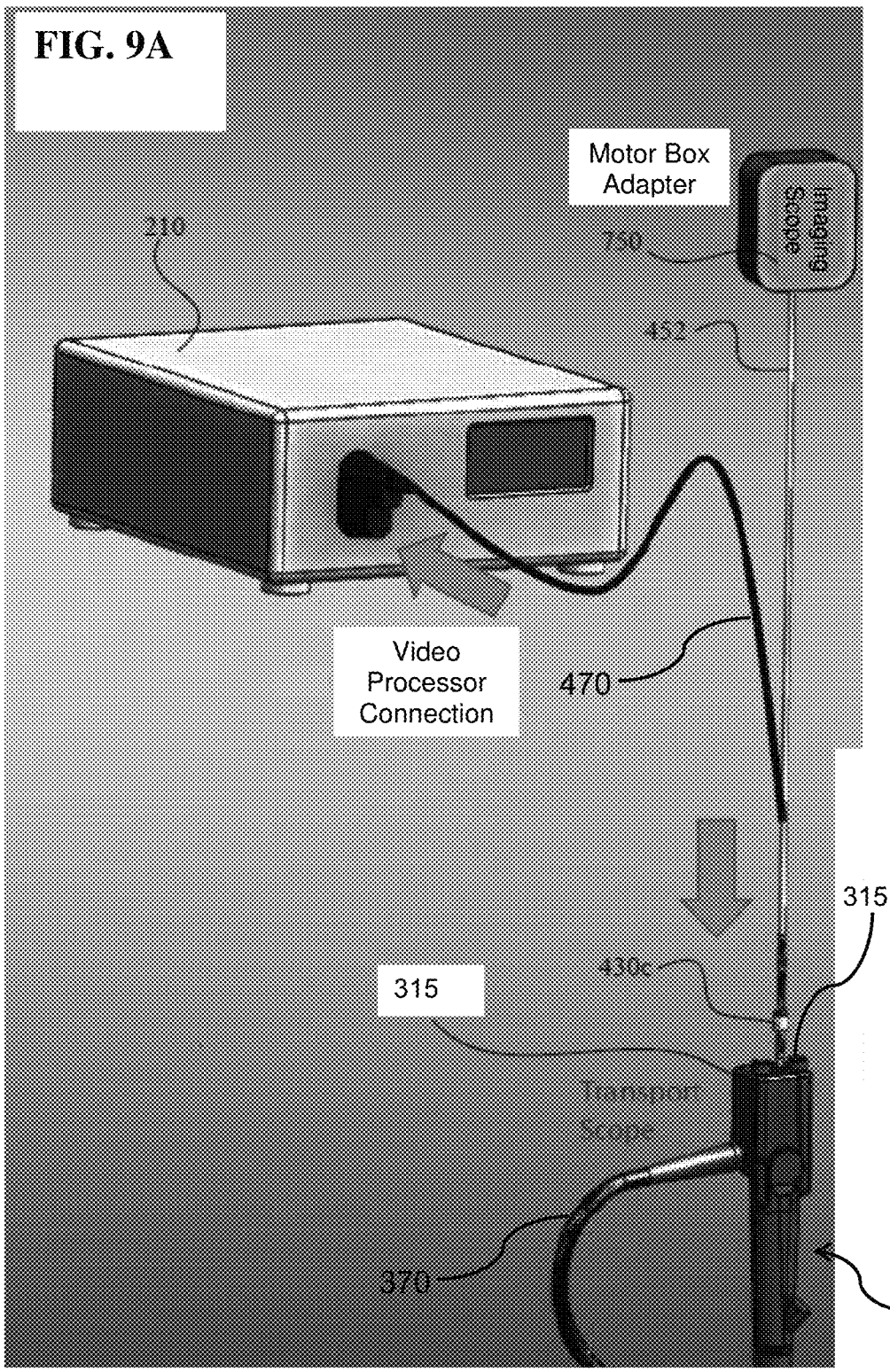

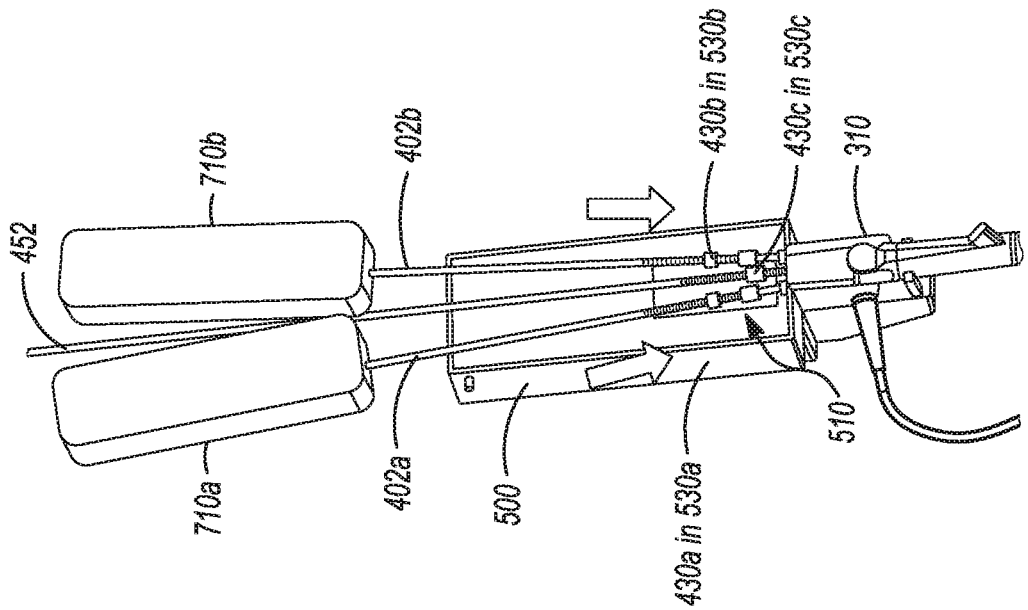
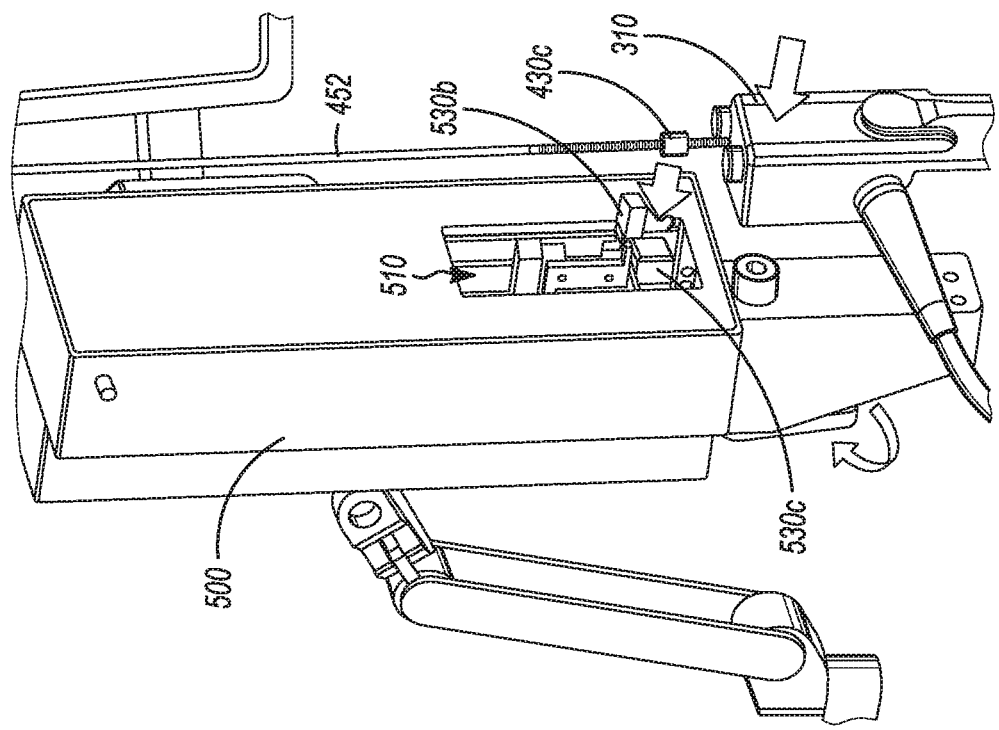
FIG. 10B
FIG. 10A

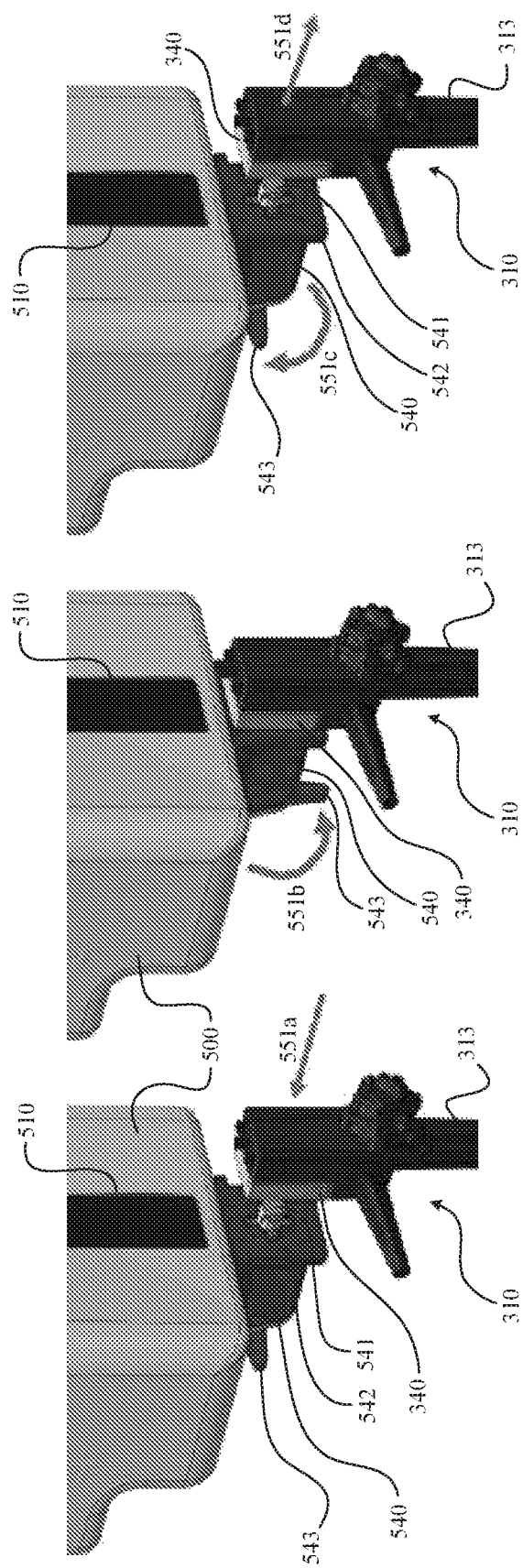

ENHANCED FLEXIBLE ROBOTIC ENDOSCOPY APPARATUS

CROSS-REFERENCE TO RELATED APPLICATIONS

This application is a U.S. National Phase application, under 35 U.S.C. § 371, of International Application no. PCT/SG2015/050042, with an international filing date of Mar. 19, 2015, which is hereby incorporated by reference for all purposes.

TECHNICAL FIELD

The present disclosure relates to an enhanced flexible robotic endoscopy apparatus having a main body and flexible elongate shaft. The main body includes a housing having a proximal end that carries a plurality of insertion inlets through which a plurality of endoscopy instrument channels are accessible; and the flexible elongate shaft has a proximal end extending away from the distal end of the main body to a distal end, and a plurality of channels therebetween for carrying portions of flexible elongate assemblies insertable into the plurality of channels of the flexible elongate shaft through the inlets.

BACKGROUND

Surgical robotics has enabled a revolution in surgical techniques, particularly with respect to minimally invasive surgery. The advent of flexible robotic endoscopy has enabled procedures such as Natural Orifice Transluminal Endoscopic Surgery (NOTES) or "incisionless" surgical procedures that do not require a percutaneous access site into the body, whereby a flexible robotic endoscope is inserted into a natural orifice of a subject, such as the subject's mouth, and is further navigated within or along a natural internal passageway such as portions of the subject's digestive tract until a distal end of the endoscope is positioned at or proximate to a target site of interest within the subject. Once the distal end of the endoscope is positioned at the target site, a surgical intervention can be performed by way of one or more robot arms and corresponding end effectors that are carried by the endoscope, and which are translatable and manipulable beyond the endoscope's distal end under robotic control in response to surgeon interaction with a control console. Representative examples of a master-slave flexible robotic endoscope system are described in (a) International Patent Application No. PCT/SG2013/000408; and/or (b) International Patent Publication No. WO 2010/138083.

SUMMARY OF THE INVENTION

Technical Problems

In current flexible robotic endoscopy systems, a number of flexible endoscopic instruments or instrument assemblies such as robotic arms with corresponding end effectors and an imaging assembly probe for capturing images of the end effector(s), are known. The flexible endoscopic instruments are disposable, and can be inserted into or withdrawn from the flexible robotic endoscopy system.

Within an operating theater, it is desirable to enhance or maximize the convenience and rapidity of setup/assembly and disassembly of the flexible robotic endoscopy system, while simultaneously ensuring that the overall manner in which the system is setup enables highly precise spatial and temporal control over the robotic elements of the system. Furthermore, under operating theater conditions, a clinician will need to quickly install new flexible endoscopic instruments or replace currently installed flexible endoscopic instruments with new or other types of flexible endoscopic instruments.

Unfortunately, existing systems fail to adequately consider the impact of the manner in which the flexible endoscopic system is setup, and the manner in which flexible endoscopic instruments are inserted into and through the flexible robotic endoscopy system and the resulting forces on internal portions of the endoscopic instruments have upon the ability of the system to reliably spatially and temporally control the end effector(s) with maximum precision.

Advantageous Effects

According to embodiments of the present disclosure, a plurality of flexible robotic elongate assemblies such as actuation assemblies and a flexible imaging endoscopy assembly can be inserted into a transport endoscope and a flexible elongate shaft thereof quickly and conveniently, in a manner that facilitates enhanced precision spatial and temporal control of the robotic elements of such assemblies.

According to embodiments of the present disclosure, the transport endoscope is easily and securely detachably engaged with the docking station, for instance, by way of the joint member. The grip on the main body of the transport endoscope is typically positioned toward the distal end of the main body, and the joint member is positioned toward the proximal end of the main body. A clinician such as an endoscopist can hold the grip on the main body, and rapidly and conveniently engage or disengage the main body from the docking station. It is not necessary for the clinician to change or release the grip of the main body from their hand to engage or disengage the transport endoscope with or from the docking station.

BRIEF DESCRIPTION OF THE DRAWINGS

FIGS. 9A-9C are schematic illustrations showing imaging endoscope assembly insertion into a transport endoscope, imaging connector assembly coupling to an imaging subsystem, imaging input adapter coupling to an imaging output adapter of a motorbox, and an endoscopy support function connector assembly coupling to a valve control unit in accordance with an embodiment of the present disclosure.

FIGS. 10A-10B are schematic illustrations showing transport endoscope docking to a docking station, with portions of outer sleeves/coils of actuation assemblies and an outer sleeve of an imaging endoscope assembly inserted into the transported endoscope, and such outer sleeves securely coupled to a translation unit of the docking station.

FIGS. 11A-11C illustrate a docking mechanism by which the transport endoscope can be matingly engaged with docking station in accordance with an embodiment of the present disclosure.

DETAILED DESCRIPTION OF EXAMPLE EMBODIMENTS

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range, for instance, within +/−20%, +/−15%, +/−10%, or +/−5%.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Embodiments of the present disclosure are directed to master-slave flexible robotic endoscopy systems, which include a master-side system and a slave-side system that is controllable or controlled by the master-side system. Also, the embodiments of the present disclosure provide enhanced mechanisms or structures of the slave or slave-side system.

Figure 1A:
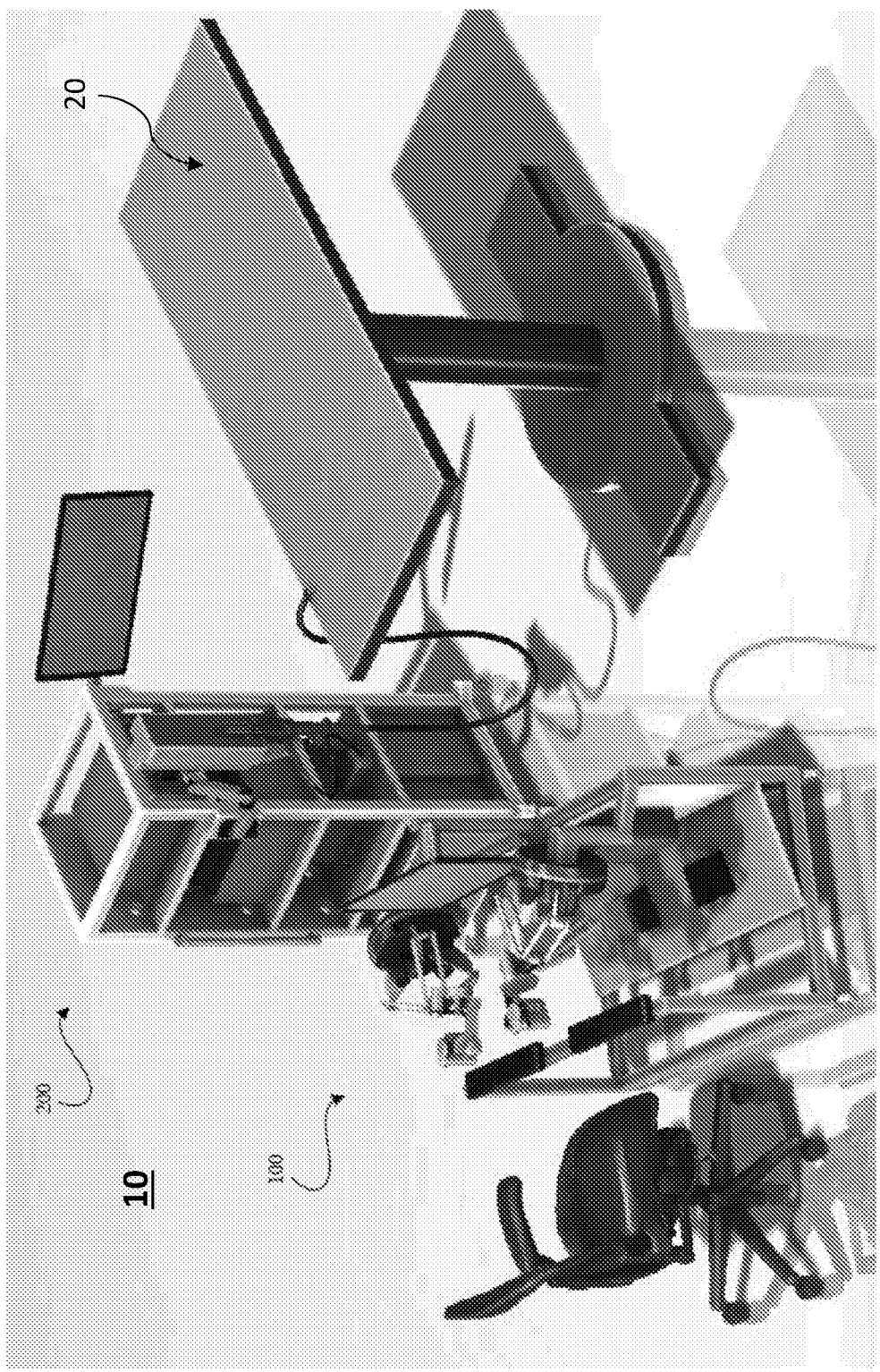
FIGS. 1A and 1B are schematic illustrations of a master-slave flexible robotic endoscopy system in accordance with an embodiment of the disclosure.
Figure 1B:
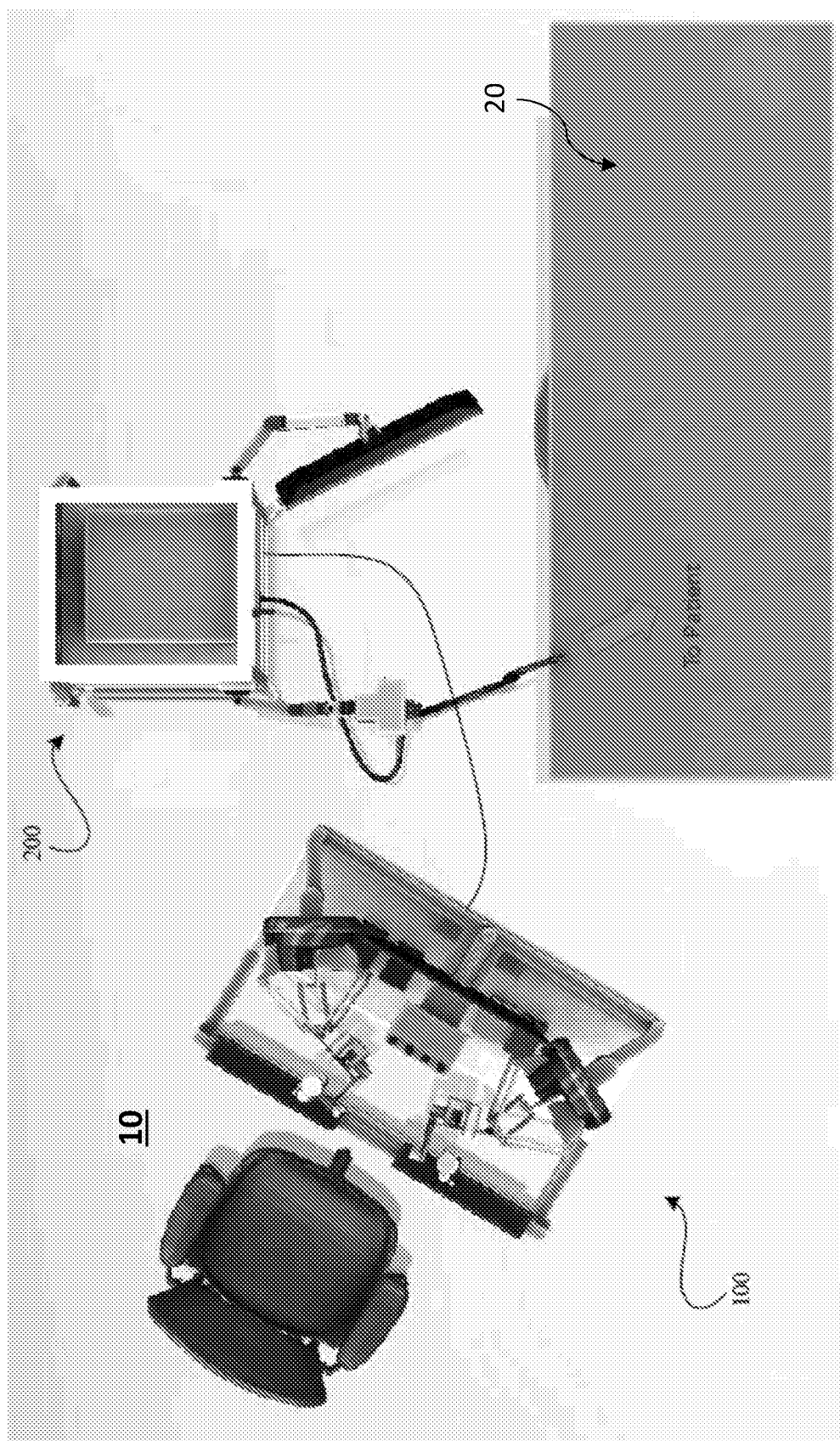

FIGS. 1A and 1B are schematic illustrations of a master-slave flexible robotic endoscopy system 10 in accordance with an embodiment of the disclosure. In an embodiment, the system 10 includes a master or master-side system 100 having master-side elements associated therewith, and a slave or slave-side system 200 having slave-side elements associated therewith.

Figure 5:
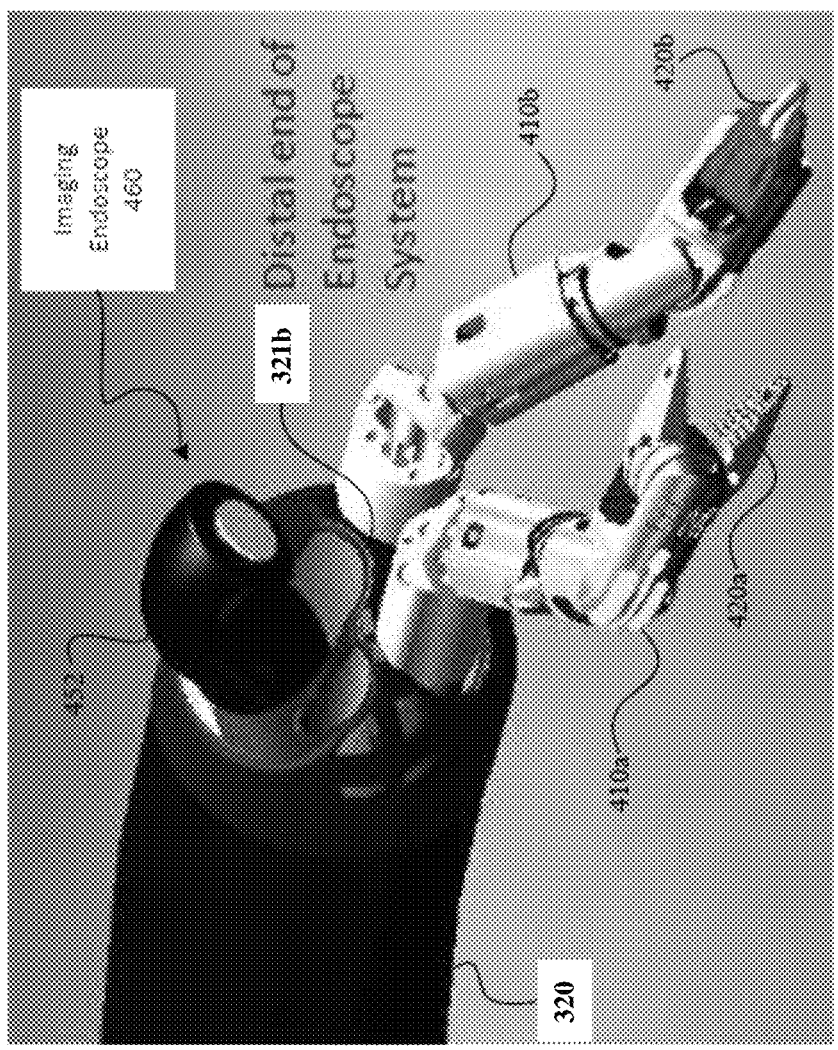
FIG. 5 is a schematic illustration of a pair of robotic arms and corresponding end effectors carried thereby, as well as an imaging endoscope, positioned in an environment beyond a distal end of a transport endoscope in accordance with an embodiment of the present disclosure.

With further reference to FIG. 5 which shows a distal end of endoscopy apparatus disposed at a slave or slave-side system 200, in various embodiments, the master system 100 and the slave system 200 are configured for signal communication with each other such that the master system 100 can issue commands to the slave system 200 and the slave system 200 can precisely control, maneuver, manipulate, position, and/or operate (a) a set of robotic arms 400a,b and corresponding end effectors 410a,b carried or supported by a transport endoscope 300 of the slave system 200, and possibly (b) an imaging endoscope or imaging probe member 460 carried or supported by the transport endoscope 300, in response to master system inputs. The master and slave systems 100, 200 can further be configured such that the slave system 200 can dynamically provide tactile/haptic feedback signals (e.g., force feedback signals) to the master system 100 as the robotic arms 410a,b and/or end effectors 420a-b associated therewith are positioned, manipulated, or operated. Such tactile/haptic feedback signals are correlated with or correspond to forces exerted upon the robotic arms 410a,b and/or end effectors 420a-b within an environment in which the robotic arms 410a,b and end effectors 420a,b reside.

Turning back to FIGS. 1A and 1B, various embodiments in accordance with the present disclosure are directed to surgical situations or environments, for instance, Natural Orifice Transluminal Endoscopic Surgery (NOTES) procedures performed upon a patient or subject while they are disposed on a surgical table or platform 20. In such embodiments, at least portions of the slave system 200 are configured to reside within an Operating Theatre (OT) or Operating Room (OR). Depending upon embodiment details, the master system 100 can reside within or outside of (e.g., near or remote from) the OT/OR. Communication between the master system 100 and the slave system 200 can occur directly (e.g., through a set of local communication lines, and/or local wireless communication), or indirectly by way of one or more networks (e.g., a Local Area Network (LAN), a Wide Area Network (WAN), and/or the Internet) in accordance with embodiment details.

Figure 2:
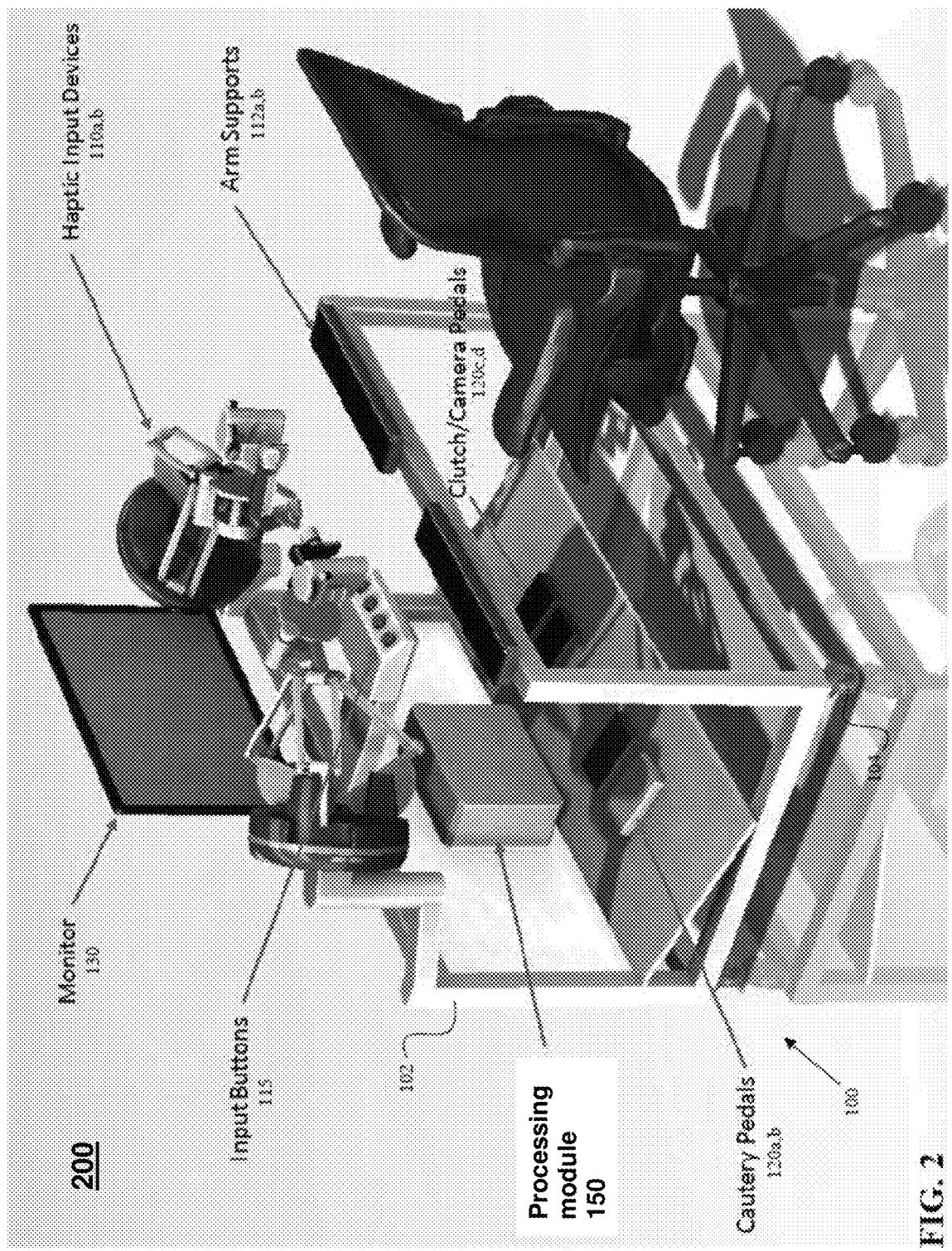
FIG. 2 is a schematic illustration of a master system in accordance with an embodiment of the present disclosure.

FIG. 2 is a schematic illustration of a master system 100 in accordance with an embodiment of the present disclosure. In an embodiment, the master system 100 includes a frame or console structure 102 that carries left and right haptic input devices 110a,b; a set of additional/auxiliary hand-operated input devices/buttons 115; a set of foot operated controls or pedals 120a-d; a display device 130; and a processing module 150. The frame/console structure 102 can include a set of wheels 104 such that the master system 100 is readily portable/positionable within an intended usage environment (e.g., an OT/OR, or a room external to or remote therefrom); and a set of arm supports 112. During a representative endoscopy procedure, a surgeon positions or seats themselves relative to the master system 100 such that their left and right hands can hold or interact with the left and right haptic input devices 110a,b, and their feet can interact with the pedals 120a-d. The processing module 150 processes signals receive from the haptic input devices 110a,b, the additional/auxiliary hand-operated input devices 115, and the pedals 120a-d, and issues corresponding commands to the slave system 200 for purpose of manipulating/positioning/controlling the robotic arms 410a,b and the end effectors 420a,b corresponding thereto, and possibly manipulating/positioning/controlling the imaging endoscope 460. The processing module 150 can additionally receive tactile/haptic feedback signals from the slave system 200, and conveys such tactile/haptic feedback signals to the haptic input devices 110a,b. The processing module 150 includes computing/processing and communication resources (e.g., one or more processing units, memory/data storage resources including Random Access Memory (RAM) Read-only Memory (ROM), and possibly one or more types of disk drives, and a serial communication unit and/or network communication unit) in a manner readily understood by one having ordinary skill in the relevant art.

Figure 3:
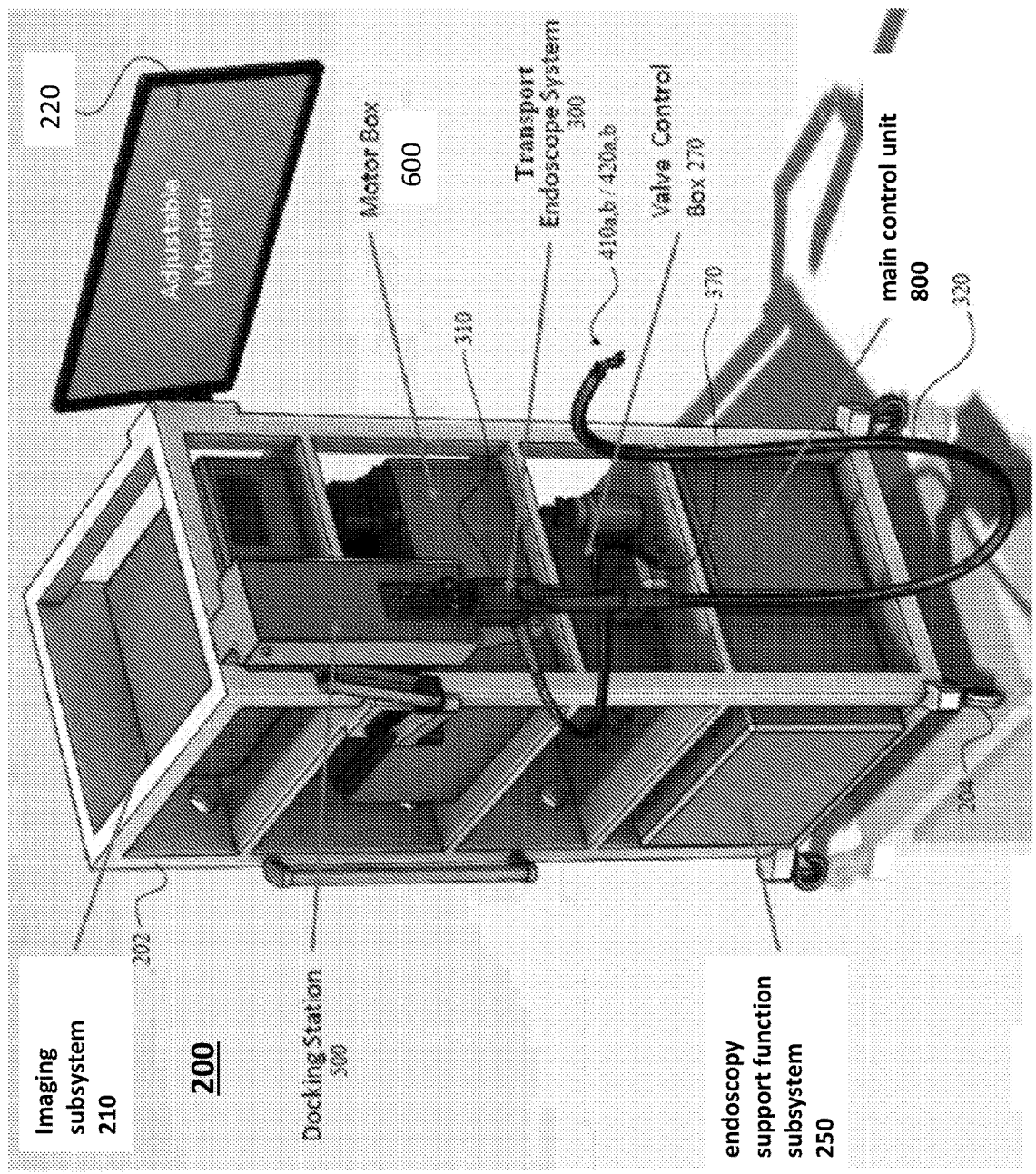
FIG. 3 is a schematic illustration of a slave system in accordance with an embodiment of the present disclosure.

FIG. 3 is a schematic illustration of a slave system 200 in accordance with an embodiment of the present disclosure. In an embodiment, the slave system 200 includes a transport endoscope 300 having a flexible elongate shaft 320; a docking station 500 to which the transport endoscope 300 can be selectively/selectably coupled (e.g., mounted/docked and dismounted/undocked); an imaging subsystem 210; an endoscopy support function subsystem 250 and an associated valve control unit 270; an actuation unit or motorbox 600; and a main control unit 800. In several embodiments, the slave system 200 additionally includes a patient-side cart, stand, or rack 202 configured for carrying at least some slave system elements. The patient side cart 202 typically includes wheels 204 to facilitate easy portability and positioning of the slave system 200 (e.g., at a desired location within an OT/OR).

In brief, the imaging subsystem 210 facilitates the provision or delivery of illumination to the imaging endoscope 460, as well as the processing and presentation of optical signals captured by the imaging endoscope 460. The imaging subsystem 210 includes an adjustable display device 220 configured for presenting (e.g., on a real-time basis) images captured by way of the imaging endoscope 460, in a manner readily understood by one having ordinary skill in the relevant art. The endoscopy support function subsystem 250 in association with the valve control unit 270 facilitates the selective controlled provision of insufflation or positive pressure, suction or negative/vacuum pressure, and irrigation to the transport endoscope 300, as also readily understood by one having ordinary skill in the relevant art. The actuation unit/motorbox 600 provides a plurality of actuators or motors configured for driving the robotic arms 410a,b and the end effectors 420a,b under control of the main control unit 800, which includes a set of motor controllers.

The main control unit 800 additionally manages communication between the master system 100 and the slave system 200, and processes input signals received from the master system 100 for purpose of operating the robotic arms 410a,b and end effectors 420a,b in a manner that directly and precisely corresponds to surgeon manipulation of the master system's haptic input devices 110a,b. In multiple embodiments, the main control unit 800 additionally generates the aforementioned tactile/haptic feedback signals, and communicates such tactile/haptic feedback signals to the master system 100 on a real-time basis. In several embodiments, the tactile/haptic feedback signals can be generated by way of sensors that are disposed proximal to the flexible elongate shaft 320 and/or body 310 (e.g., sensors that reside in the motorbox 600), without use or exclusive of sensors carried within or distal to the flexible elongate shaft 320 and/or body 310 (e.g., sensors carried on, near, or generally near a robotic arm 410 or end effector 420). Representative manners of generating tactile/haptic feedback signals are described in detail in International Patent Application No. WO 2010/138083. The main control unit 800 includes signal/data processing, memory/data storage, and signal communication resources (e.g., one or more microprocessors, RAM, ROM, possibly a solid state or other type of disk drive, and a serial communication unit and/or network interface unit) in a manner readily understood by one having ordinary skill in the relevant art.

Figure 4:
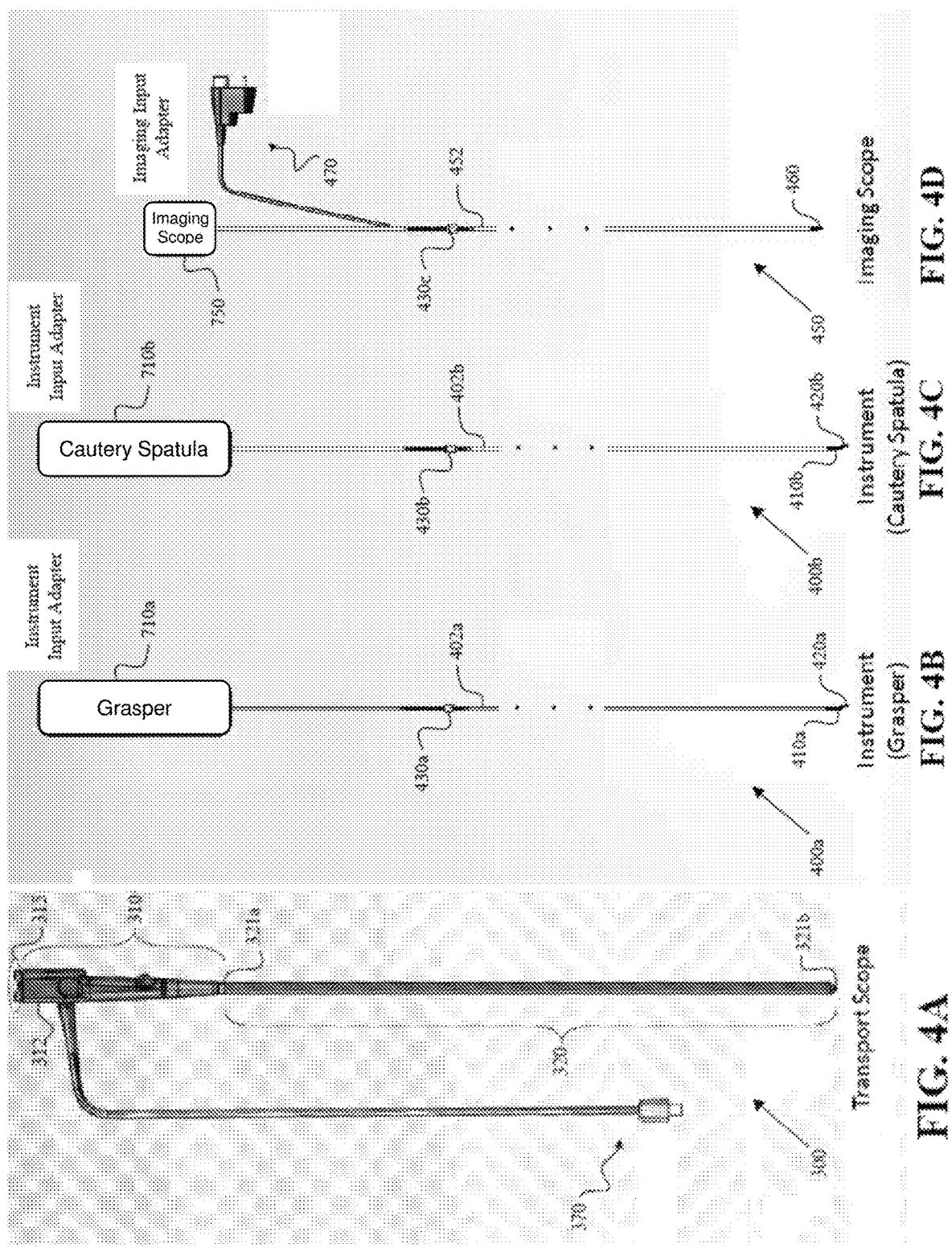
FIGS. 4A-4D are schematic illustrations of a representative transport endoscope, first and second actuation assemblies, and an imaging endoscopy assembly, respectively, in accordance with an embodiment of the present disclosure.

FIG. 4A is an illustration of a representative transport endoscope 300 and FIGS. 4B-4D are illustrations of representative flexible elongate assemblies which can be inserted to or withdrawn from the transport endoscope 300 in accordance with an embodiment of the disclosure. The flexible elongate assemblies may comprise the actuation assemblies 400a, 400b as shown in FIGS. 4B-4C and a flexible imaging endoscope assembly 450 as shown in FIG. 4D.

The actuation assemblies 400a, 400b may include or be robotic surgical instruments, e.g., a grasper 400a as shown in FIG. 4B or e.g., a cautery spatula 400b as shown in FIG. 4C in accordance with an embodiment of the disclosure. Also, flexible imaging endoscope assembly 450 may be an imaging endoscope probe in accordance with an embodiment of the disclosure as shown in FIG. 4D.

With reference to FIG. 4A, the transport endoscope 300 comprises a main body 310 at a proximal end and a flexible elongate shaft 320 toward a distal end. In a preferred embodiment, the main body 310 may be made of rigid material(s) such as hard plastics or metals and the flexible elongate shaft 320 is made of flexible materials such as rubber, rubber-like, and/or soft plastic materials.

The main body 310 includes or defines a proximal portion, border, surface, or end of the transport endoscope 300, and provides a plurality of insertion inlets 315 through which channels that extend within and along the flexible elongate shaft 320 are accessible. The main body 310 comprises a proximal end portion or proximal end 311a and a distal end portion or distal end 311b, and a housing 312 that extends between or from the proximal end 311a to the distal end 311b. The housing 312 comprises a plurality of surfaces and the plurality of insertion inlets 315. The plurality of insertion inlets 315 is carried by the proximal end 311a of the main body 310, for instance, such that the plurality of insertion inlets 315 resides on at least one surface of the housing 312 at the main body's proximal end 311a (e.g., a top surface or a set of top surfaces of the housing 312 at the main body's proximal end 311a).

In several embodiments, the main body 310 additionally provides a control interface for the transport endoscope 300, by which an endoscopist can exert navigational control over the flexible elongate shaft 320. For instance, the main body 310 can include a number of control elements, such as one or more buttons, knobs, switches, levers, joysticks, and/or other control elements to facilitate endoscopist control over transport endoscope operations, in a manner readily understood by one having ordinary skill in the relevant art.

The flexible elongate shaft 320 is configured to extend away from the distal end 311b of the main body 310 and terminate at a distal end of the transport endoscope 300. The flexible elongate shaft 320 comprises a proximal end 321a, a distal end 321b, a central axis (not shown) and a plurality of channels therewithin for carrying portions of flexible elongate assemblies and an opening disposed at the flexible elongate shaft's distal end 321b for each of the plurality of channels.

The plurality of channels may comprise a set of instrument channels which carry actuation assemblies 400a, 400b as shown in FIGS. 4B-4C. In various embodiments, the channels may also comprise passages for enabling the delivery of insufflation or positive pressure, suction or vacuum pressure, and irrigation to an environment in which the distal end of the flexible elongate shaft 320 resides.

Each actuation assembly 400a,b typically corresponds to a given type of endoscopic tool. For instance, in a representative implementation, a first actuation assembly 400a can carry a first robotic arm 410a having a grasper or similar type of end effector 420a as shown in FIG. 4B; and a second actuation assembly 400b can carry a second robotic arm 410b having a cautery spatula or similar type of cauterizing end effector 420b as shown in FIG. 4C.

In an embodiment indicated in FIGS. 4B-4C, a given actuation assembly 400a,b includes a robot arm 410a,b and its corresponding end effector 420a,b; a flexible elongate outer sleeve and/or coil 402a,b that internally carries a plurality of tendon/sheath elements, such that tension or mechanical forces can be selectively applied to particular tendon elements for precisely manipulating and controlling the operation of the robot arm 410a,b and/or the end effector 420a,b; and an instrument input adapter 710a,b by which tendons within the outer sleeve 402a,b can be mechanically coupled to corresponding actuators within the motorbox 600, as further detailed below. Representative types of tendon/sheath elements, robotic arms 410a,b, and end effectors 420a,b, as well as representative manners in which tendon elements can couple to and control portions of a robot arm 410a,b (e.g., joints/joint primitives) and/or a corresponding end effector 420a,b to provide maneuverability/manipulability relative to available DOFs are described in detail in (a) International Patent Application No. PCT/SG2013/000408; and/or (b) International Patent Publication No. WO 2010/138083. A given tendon and its corresponding sheath can be defined as a tendon/sheath element.

In FIGS. 4B and 4C, the robot arm 410a,b, end effector 420a,b, and portions of the outer sleeve/coil 402a,b can be inserted into an instrument channel of the flexible elongate shaft 320, such that the robot arm 410a,b and the end effector 420a,b reach or approximately reach, and can extend a predetermined distance beyond, the distal end 321b of the flexible elongate shaft 320. As described in detail below, the actuation assembly's outer sleeve/coil 402a,b, and hence the robot arm 410a,b and end effector 420a,b, can be selectively longitudinally translated or surged (i.e., displaced distally or proximally with respect to the distal end 321b of the flexible elongate shaft 320) by way of a translation unit such that the proximal-distal positions of the robotic arm 410a,b and the end effector 420a,b relative to the distal end 321b of the flexible elongate shaft 320 can be adjusted within an environment beyond the distal end 321b of the flexible elongate shaft 320, up to a predetermined maximum distance away from the distal end 321b of the flexible elongate shaft 320, for purpose of carrying out an endoscopic procedure. In a number of embodiments, an actuation assembly 400 can be disposable.

In particular embodiments, the actuation assembly 400a,b includes a collar element, collet, or band 430a,b that surrounds at least a portion of the outer sleeve/coil 402a,b at a predetermined distance away from the distal tip of the end effector 420a,b. As detailed below, the collar element 430a,b is designed to matingly engage with a receiver of the translation mechanism, such that longitudinal/surge translation of the collar element 430a,b across a given distance relative to the distal end of the flexible elongate shaft 320 results in corresponding longitudinal/surge translation of the robotic arm 410a,b and end effector 420a,b.

In several embodiments, the plurality of channels provided within the flexible elongate shaft 320 additionally include an imaging endoscope channel, which is configured for carrying portions of a flexible imaging endoscope assembly 450 as shown in FIG. 4D that can be inserted into and/or withdrawn from the transport endoscope 300. Referring to FIG. 4D, in a manner analogous or generally analogous to that described above for the actuation assembly 400a,b, in an embodiment the imaging endoscope assembly 450 includes a flexible outer sleeve, coil, or shaft 452 that surrounds or forms an outer surface of the flexible imaging endoscope 460; an imaging input adapter 750 by which a set of tendons corresponding to or within the imaging endoscope 460 can be mechanically coupled to corresponding actuators within the motorbox 600 such that a distal portion of the imaging endoscope 460 can be selectively maneuvered or positioned in accordance with one or more DOFs (e.g., heave and/or sway motion) within an environment at, near, and/or beyond the distal end 321b of the flexible elongate shaft 320; and an imaging connector assembly 470 by which optical elements (e.g., optical fibers) of the imaging endoscope 460 can be optically coupled to an image processing unit of the imaging subsystem 210. For instance, the imaging endoscope 460 can include or be coupled to tendons such that a distal end or face of the imaging endoscope 460 can selectively/selectably capture anterograde and retrograde images of the robotic arms 410a,b and end effectors 420a,b during an endoscopic procedure. Representative embodiments of imaging endoscopes and control elements such as tendons associated therewith that can be incorporated into an imaging endoscope assembly 450 in accordance with an embodiment of the present disclosure are described in International Patent Application No. PCT/SG2013/000408 hereto. In some embodiments, the imaging endoscope assembly 450 can be disposable.

In a manner identical, essentially identical, or analogous to that for the actuation assembly 400a,b, the outer sleeve 452 of the imaging endoscope assembly 450, and hence the distal end of the imaging endoscope 460, can be selectively longitudinally translated/surged relative to the distal end 321b of the flexible elongate shaft 320 by way of the translation mechanism, such that the longitudinal or proximal-distal position of the imaging endoscope 460 can be adjusted at, near, and/or beyond the distal end of the flexible elongate shaft 320 across a predetermined proximal-distal distance range in association with an endoscopic procedure.

In a number of embodiments, the imaging endoscope assembly 450 includes a collar element 430c that surrounds at least portions of the imaging endoscope assembly's outer sleeve 452 at a predetermined distance away from the distal end 460 of the imaging endoscope 450. The collar element 430c is configured for mating engagement with a receiver or receiving structure of the translation mechanism, such that longitudinal/surge displacement of the collar element 430c across a given distance relative to the distal end of the flexible elongate shaft 320 results in corresponding longitudinal/surge displacement of the distal end of the imaging endoscope 460.

As a result, in several embodiments the transport endoscope 300 may have two robotic arms 410a,b and corresponding end effectors 420a,b carried thereby, as well as a flexible imaging endoscope, positioned in an environment beyond a distal end of a transport endoscope in accordance with an embodiment of the present disclosure as shown in FIG. 5.

In an embodiment, the flexible elongate assemblies comprising actuation assemblies 400a, 400b and a flexible imaging endoscope assembly 450 may be insertable to the plurality of channels within the flexible elongate shaft 320 through the insertion inlets 315, with axes of the flexible elongate assemblies being parallel to the central axis of the flexible elongate shaft. In other words, the actuation assemblies 400a,b of FIGS. 4B and 4C and the flexible imaging endoscope assembly 450 of FIG. 4D are configured for insertion into and withdrawal from instrument channels and an imaging endoscope channel of the transport endoscope 300, respectively, with axes of the actuation assemblies 400a,b and axis of the flexible imaging endoscope assembly being parallel to the central axis of the flexible elongate shaft 320 as shown in FIG. 9A, or parallel to the instrument channels or the imaging endoscope channel carried by the flexible elongate shaft 320 as readily understood by one having ordinary skill in the relevant art. Correspondingly or equivalently, each of the insertion inlets 315 can have an insertion axis corresponding thereto, along which an actuation assembly 400 or the flexible imaging endoscope assembly 450 is insertable, such that the insertion axes of the insertion inlets 315 are parallel to the central axis of the flexible elongate shaft 320 at the proximal region or end of the flexible elongate shaft 320. For a given insertion inlet 315, a plane of an aperture or opening of the insertion inlet 315 into and through which an actuation assembly 400 or the flexible imaging endoscope assembly 450 is insertable/inserted is transverse or perpendicular to its insertion axis.

Referring further to FIGS. 4B-4C, when the actuation assemblies 400a,b and the flexible imaging endoscope assembly 450 have been fully inserted into the transport endoscope 300 prior to their manipulation in an environment external to the distal end of the flexible elongate shaft 320 during an endoscopic procedure, each collar element 430a-c remains outside of and at least slightly away from the flexible elongate shaft 320, and in various embodiments outside of and at least slightly away from the transport endoscope's main body 310, such that longitudinal translation or surge motion of a given collar element 430a-c across a predetermined proximal-distal distance range can freely occur by way of the translation unit, without interference from the flexible elongate shaft 320 and/or main body 310. Thus, the outer sleeve/coil 402a,b of each actuation assembly 400a,b must distally extend a sufficient length away from a distal border of its collar element 430a,b, such that the end effector 420a,b reaches or approximately reaches the distal end 321b of the flexible elongate shaft 320 when the collar element 430a,b resides at a most-proximal position relative to the translation unit. Similarly, the imaging endoscope assembly's outer sleeve 452 must distally extend a sufficient length away from its collar element 430c such that the distal end of the imaging endoscope 460 resides at an intended position at, proximate to, or near the distal end 321b of the flexible elongate shaft 320 when the collar element 430c is at a most-proximal position relative to the translation unit.

Referring back to FIG. 4A, the transport endoscope 300 may additionally include an endoscopy support function connector assembly 370 by which the transport endoscope's main body 310 can be coupled to the endoscopy support function subsystem 250, in a manner readily understood by one having ordinary skill in the relevant art.

Figure 6:
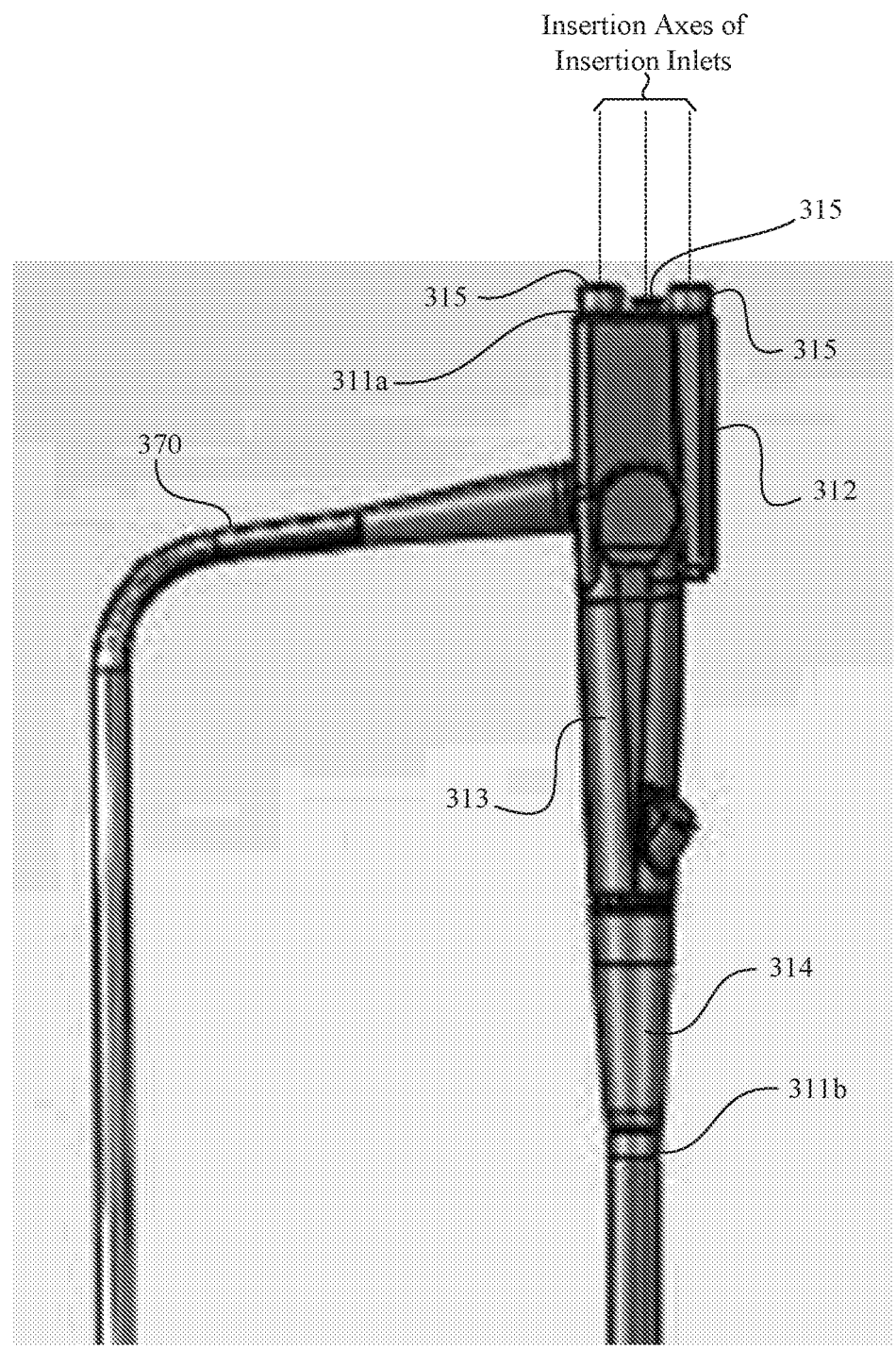
FIG. 6 illustrates a representative main body 310 in accordance with an embodiment of the present disclosure more specifically.

FIG. 6 illustrates a representative main body 310 in accordance with an embodiment of the present disclosure more in details. As shown in FIG. 6, the main body 310 may comprise a housing 312 that extends to the proximal end 311a, a joint member 316 on a surface of the housing 312 and a grip 313 toward the distal end 311b. Also, the main body 310 may further comprise a connector 314 which connects the main body 310 and the flexible elongate shaft 320. In a more refined or preferred embodiment, the housing 312 may include or be a cuboid or generally cuboid structure (e.g., a rectangular or generally rectangular cuboid tube), and a plurality of insertion inlets 315 may be formed on an upper and/or top surface thereof toward the proximal end of the housing 312. Also, a joint member engages the transport endoscope 300 with other elements of the slave system 200, e.g. the docking station 500, as will be described later and may be provided on a side surface of the housing 312. The grip 313 provides a region, portion, or structure that a clinician (e.g., an endoscopist or surgeon) can hold to couple or engage the transport endoscope 300 with other elements of the slave system, and spatially adjust, position, or move portions of the transport endoscope 300 relative to other elements of the slave system and/or the subject or patient.

In accordance with an embodiment of the present disclosure, a joint member 316 is located on a side surface of the housing 312 that extends from the proximal end 311a to the distal end 311b and a grip 313 is located toward the distal end of the transport endoscope 300. That is, the join member 316 is positioned toward the proximal end of the transport endoscope 300 and the grip 313 is positioned toward distal end of the transport endoscope 300 on the main body 310. Therefore, it is not necessary for a clinician to change or release the grip of main body to engage or disengage the transport endoscope 300 with or from docking station 500, or the docking mechanism as shown in FIGS. 11-14. Also, the docking mechanism can be more stable since a clinician can mount the transport endoscope 300 on the docking station 500 while the grip 313 of the main body 310 is held.

Figure 7A:
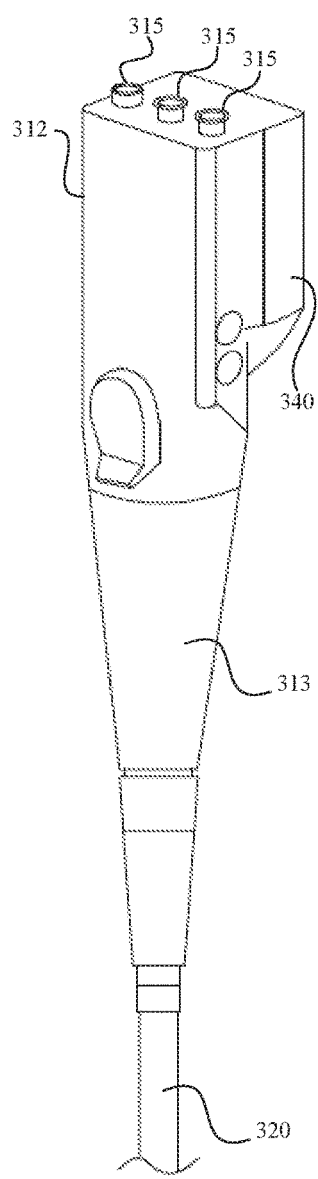
FIGS. 7A-7C illustrate arrangement of the insertion inlets in accordance with embodiments of the present disclosure.
Figure 7B:
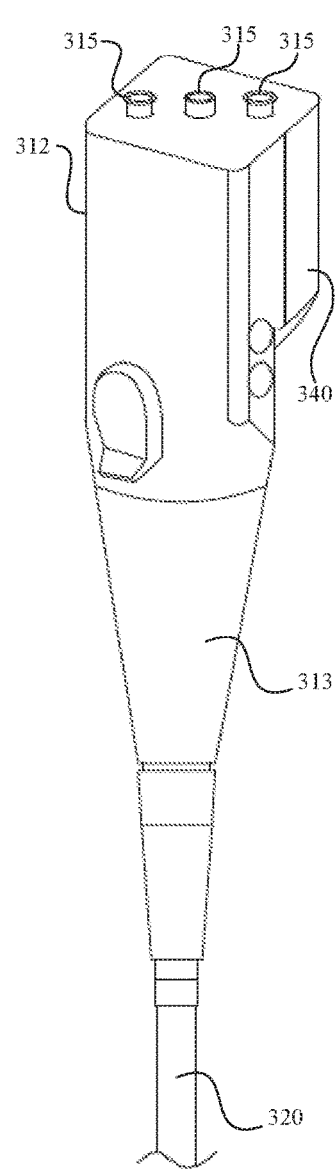
Figure 7C:
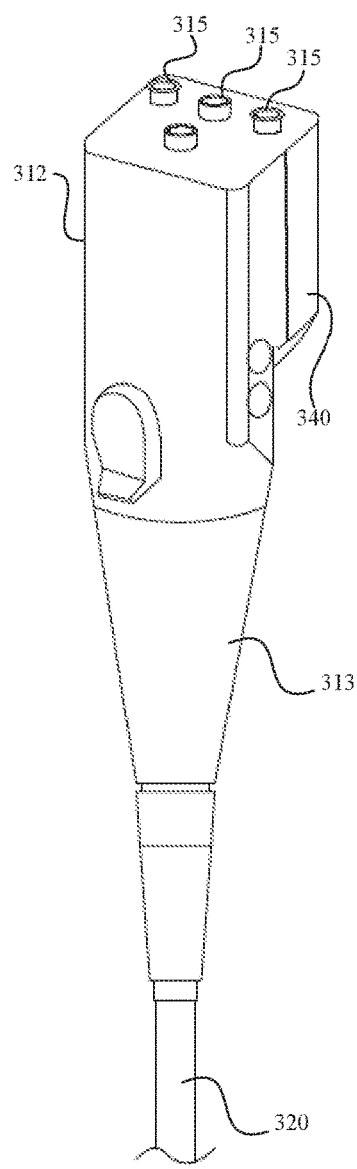

Depending upon embodiment details, the insertion inlets 315 on a surface of the main body 310 may be arranged in various ways. In a refined or preferred embodiment, the insertion inlets may be arranged such that it reduces or minimizes mechanical stress(es) on both the transport endoscope 300 and the flexible elongate assemblies including the actuation assemblies 400a, 400b and a flexible imaging endoscope assembly 450 when the clinician inserts/withdraws the flexible elongate assemblies into/from transport endoscope 300 or the slave or slave side system 200. In an embodiment, the insertion inlets 315 may be arranged in a linear or generally linear manner (e.g., along a line) as shown in FIGS. 7A-7B. Also, the insertion inlets 315 may be arranged in a line parallel to a given boundary, border, edge, or sideline of the surface, as shown in FIG. 7A, or arranged in a diagonal line as shown in FIG. 7B. Also, the number of the insertion inlets may be changed according to the number of flexible endoscope assemblies to be inserted to the transport endoscope 300 as shown in FIG. 7C and the arrangement thereof may be changed accordingly.

Representative embodiments of the transport endoscope 300 are described in detail in International Patent Application No. PCT/SG2013/000408 hereto. In certain embodiments, the transport endoscope 300 can be configured for carrying another number of actuation assemblies 400. Furthermore, the cross-sectional dimensions of the transport endoscope 300, the channels/passages therein, one or more actuation assemblies 400, and/or an imaging endoscope assembly 450 can be determined, selected, or specified in accordance with a given type of surgical/endoscopic procedure and/or transport endoscope shaft size/dimensional constraints under consideration.

Figure 8B:
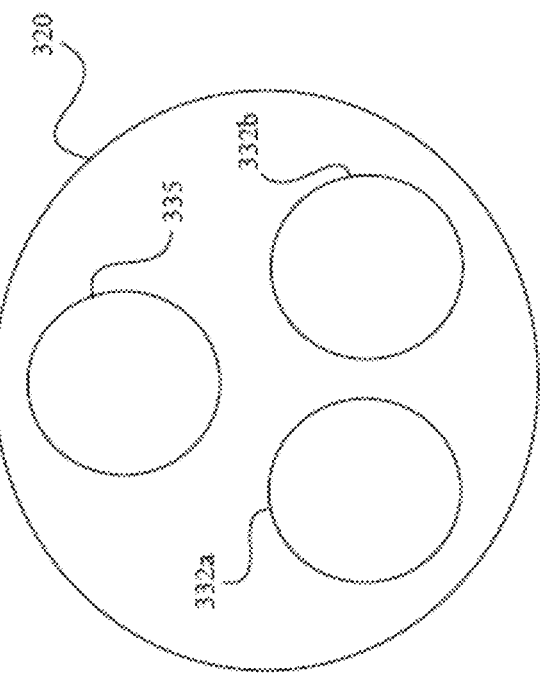
FIG. 8A is a representative cross sectional illustration of a transport endoscope shaft in accordance with an embodiment of the present disclosure and FIG. 8B is a representative cross sectional illustration of a transport endoscope shaft in accordance with another embodiment of the present disclosure.
Figure 8A:
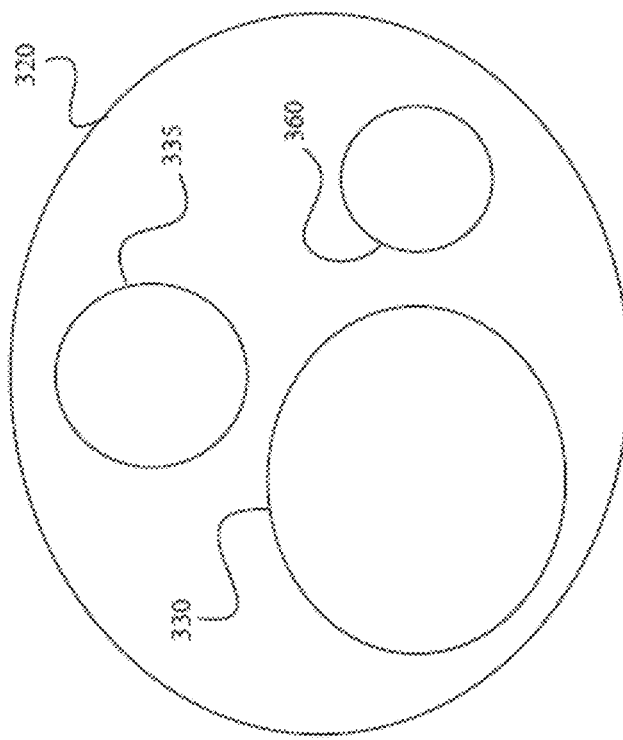

FIG. 8A is a representative cross sectional illustration of a flexible elongate shaft 320 in accordance with another embodiment of the present disclosure, in which the channels/passages therein include a primary instrument channel 330 having a large or maximal cross-sectional area/diameter configured for accommodating a high/maximum DOF robot arm/end effector 410, 420; a secondary instrument channel 360 having a smaller or significantly smaller cross-sectional area/diameter than the primary instrument channel 330, which can be configured for accommodating a manually operated conventional endoscopic instrument/tool, such as a conventional grasper (e.g., in such an embodiment, a robotic actuation assembly 400 as well as a conventional/manual actuation assembly can be inserted into corresponding ports in the transport endoscope body 310); and an imaging endoscope channel 335 configured for accommodating an imaging endoscope 460.

In an alternate embodiment, a flexible elongate shaft 320 such as that shown in FIG. 8A can exclude or omit an imaging endoscope channel 335 configured for accommodating an imaging endoscope 460, and can rather include or carry conventional endoscopic imaging elements or devices that are separate from, are not carried by, or do not form portions of an imaging endoscope 460 that is insertable into and removable from the flexible elongate shaft 320 (e.g., by way of an imaging endoscope channel 335), but which are configured to facilitate or enable the capture of images of an environment beyond the flexible elongate shaft's distal end 321b (e.g., one or more images of a robotic end effector 420 and/or a manually operated end effector) during an endoscopic procedure). Depending upon embodiment details, such conventional endoscopic imaging elements can include a set of illumination sources or devices (e.g., LEDs) and/or optical fibers corresponding thereto; an image capture device (e.g., a CCD chip and/or other type of image sensor); and a lens, at least some of which are positionally fixed with respect to the flexible elongate shaft 320, for instance, as a result of being embedded within or securely mounted on the flexible endoscope shaft 320, in a manner readily understood by individuals having ordinary skill in the art. For instance, in such an alternate embodiment, the lens can be carried by, disposed on, or mounted to the distal end 321b of the flexible elongate shaft 320 (e.g., on a vertical or angled distal face thereof), and the image sensor can be disposed behind the lens.

FIG. 8B is a representative cross sectional illustration of a flexible elongate shaft 320 in accordance with yet another embodiment of the present disclosure, in which the channels/passages therein include a first and a second instrument channel 332a,b having relatively small(er) cross-sectional areas or diameters configured for accommodating reduced/limited DOF robotic arms/end effectors 410a,b, 420a,b compared to the flexible elongate shaft embodiment of FIG. 8A; and an imaging endoscope channel 335 configured for accommodating an imaging endoscope 460.

Flexible elongate shaft embodiments such as those shown in FIGS. 8A and 8B can result in smaller overall cross-sectional areas than a flexible elongate shaft 320 described elsewhere herein, for purpose of facilitating an given type of endoscopic procedure and/or improving intubation, in a manner readily understood by one having ordinary skill in the relevant art.

Representative Procedural Setup and Interface Coupling to Motorbox

Figure 9B:
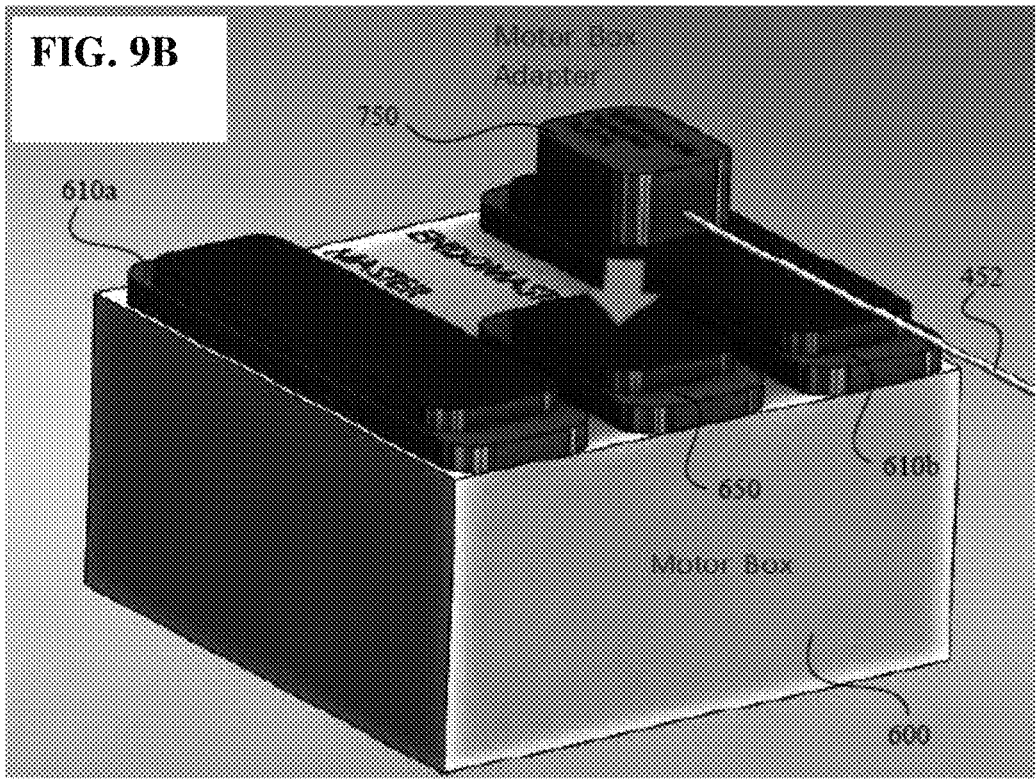
Figure 9C:
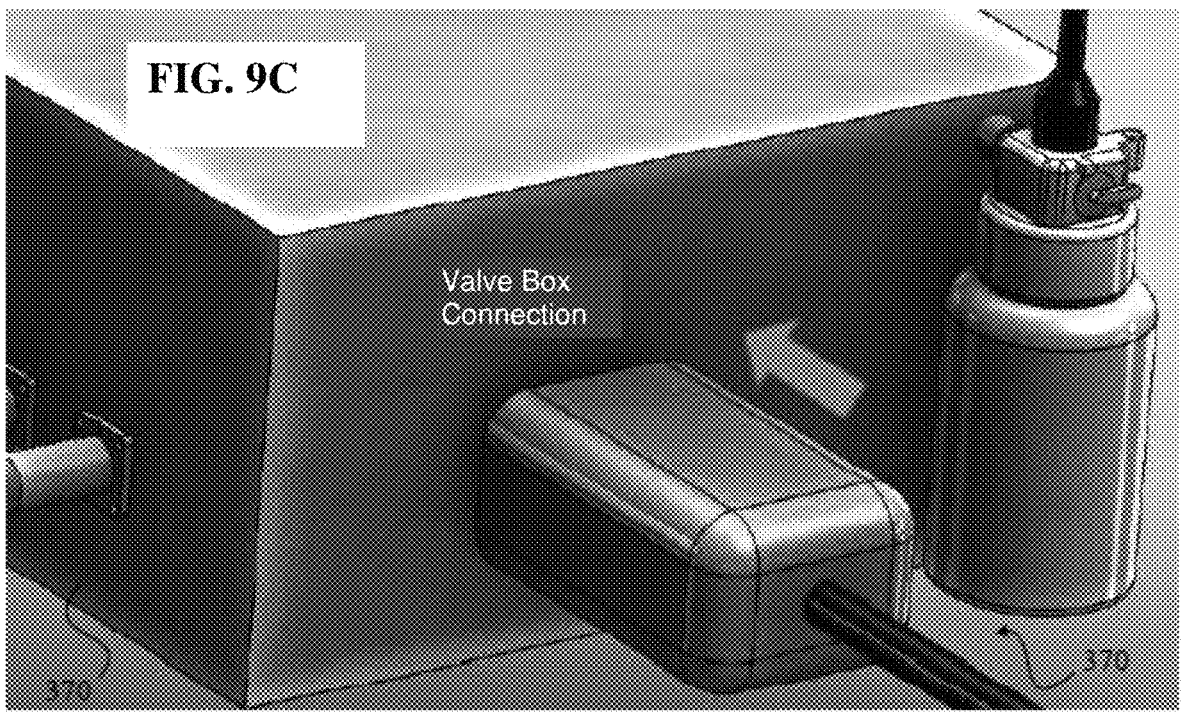

FIGS. 9A-9C illustrate portions of a representative setup procedure by which an imaging endoscope assembly 450 and a pair of actuation assemblies 400a,b can be inserted into the transport endoscope 300 and coupled to or interfaced with other portions of the slave system 200, including the motorbox 600.

As indicated in FIG. 9A, portions of the imaging endoscope assembly's outer sleeve 452 distal to the collar element 430c corresponding thereto can be inserted into one of insertion inlets 315 formed in the transport endoscope's main body 310, such that the imaging endoscope 460 can be fed into and distally advanced along the 's shaft 320 to an initial intended, default, or parked position relative to the distal end 321b thereof. As previously indicated, the collar element 430c coupled to the imaging endoscope assembly's outer sleeve 452 remains external to the flexible elongate shaft 320. More particularly, in the embodiment shown, the collar element 430c remains external to the transport endoscope's main body 310, such that the collar element 430c resides a given distance proximate to the port that received the outer sleeve 452 of the imaging endoscope assembly 450. The imaging connector assembly 470 can be coupled to the imaging subsystem 210, for instance, as in a manner indicated in FIG. 9A, as readily understood by one having ordinary skill in the relevant art, such that the imaging endoscope 460 can output illumination and capture images.

As further indicated in FIG. 9B, the imaging endoscope assembly's imaging input adapter 750 can be coupled to a corresponding imaging output adapter 650 of the motorbox 600. By way of such adapter-to-adapter coupling, a set of tendons internal to the imaging endoscope assembly's outer sleeve 452 can be mechanically coupled or linked to one or more actuators or motors within the motorbox 600. Such tendons are configured for positioning or maneuvering the imaging endoscope 460 in accordance with one or more DOFs, for instance, in a manner indicated in International Patent Application No. PCT/SG2013/000408 hereto. Consequently, the imaging endoscope 460 can be selectively positioned or manipulated in particular manners relative to the distal end 321b of the flexible elongate shaft 320 as a result of the selective application of tension to the imaging endoscope assembly's tendons by way of one or more actuators within the motorbox 600 that are associated with imaging endoscope position control.

In addition to the foregoing, the transport endoscope's support function connector assembly 370 can be coupled to the endoscopy support function subsystem 250, for instance, in a manner indicated in FIG. 9C, in order to facilitate the provision of insufflation or positive pressure, suction or negative/vacuum pressure, and irrigation in a manner readily understood by an individual having ordinary skill in the relevant art.

Figure 10C:
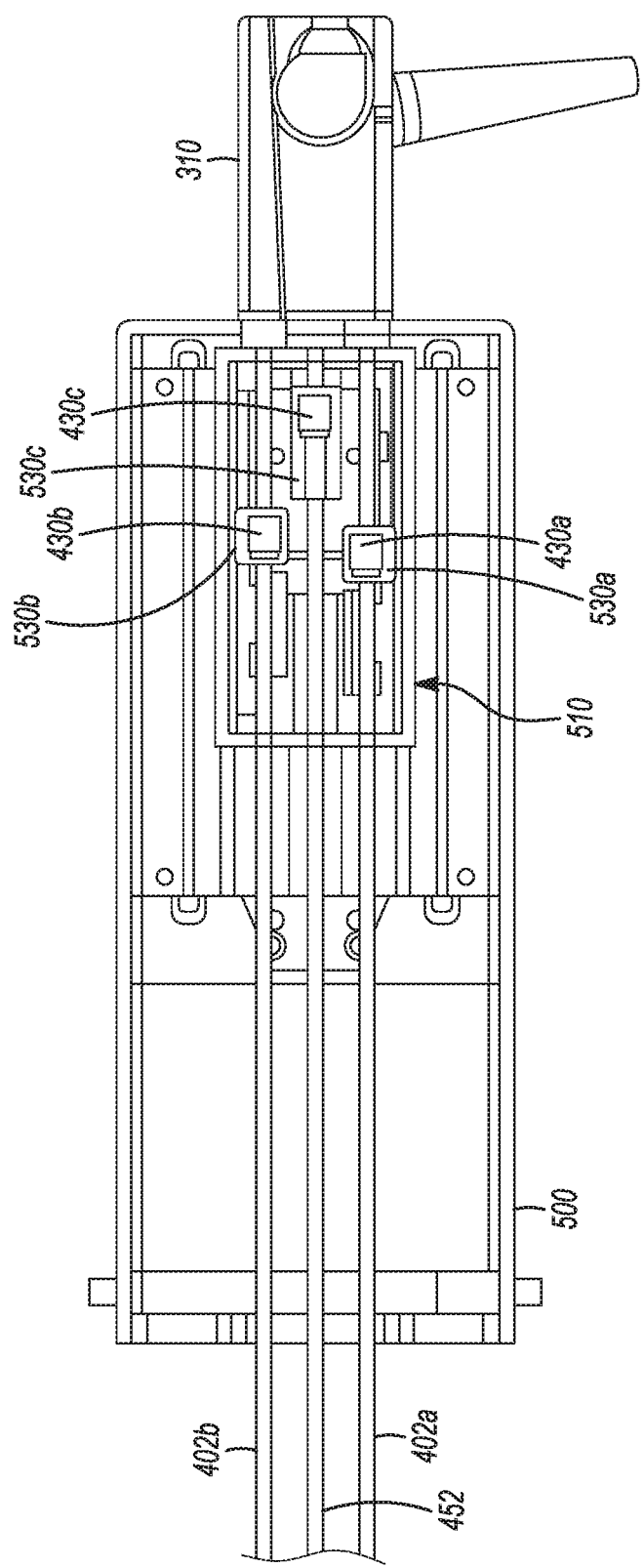
FIG. 10C is a schematic illustration showing a representative translation unit carried by the docking station, and a representative manner in which collar elements corresponding to actuation assemblies and an imaging endoscope assembly are retained by the translation unit.

FIGS. 10A-10C illustrate portions of docking mechanism by which the transport endoscope 300, and an imaging endoscope assembly 450 and a pair of actuation assemblies 400a,b can be matingly engaged with docking station 500 and translation unit 510 thereof. With reference to FIG. 10A, the transport endoscope's main body 310 can be docked or mounted to the docking station 500, and the imaging endoscope assembly's collar element 430c can be inserted into or matingly engaged with a corresponding receiver or clip 530c provided by a translation unit 510 associated with the docking station 500. Once the imaging endoscope assembly's collar element 430c is securely held by its corresponding clip 530c, the imaging endoscope assembly's sleeve 452 can be selectively/selectably longitudinally translated or surged by the translation unit 510 across a predetermined proximal-distal distance range, as further detailed below, for instance, in response to surgeon manipulation of a haptic input device 110a,b or other control (e.g., a foot pedal) at the master station 100, and/or endoscopist manipulation of a control element on the transport endoscope's main body 310 (e.g., where surgeon input can override endoscopist input directed to longitudinally translating/surging the imaging endoscope 460).

With further reference to FIG. 10B, in a manner analogous to that described above in FIG. 10A, portions of each actuation assembly 400a,b distal to a corresponding actuation assembly collar element 430a,b can be inserted into an intended/appropriately dimensioned port within the main body 310 of the transport endoscope 300. As a result, each robot arm 410a,b and end effector 420a,b can be fed into and distally advanced along the flexible elongate shaft 320 toward and to an initial intended, default, or parked position relative to the flexible elongate shaft's distal end 321b. The collar element 430a,b carried by each actuation assembly's outer sleeve/coil 402a,b remains external to the flexible elongate shaft 320, and in several embodiments external to the transport endoscope's main body 310, such that each collar element 430a,b resides a given distance proximate to the port that received the outer sleeve/coil 402a,b of the actuation assembly 400a,b.

In a manner analogous to that for the imaging endoscope assembly 450, each actuation assembly's collar element 430a,b can be inserted into or matingly engaged with a corresponding receiver or clip 530a,b provided by the translation unit 510. Once each such collar element 430a,b is securely retained by its corresponding clip 530a,b, the translation unit 510 can selectively/selectably longitudinally translate or surge one or both of the actuation assemblies 400a,b (e.g., in an independent manner) across a predetermined proximal-distal distance range, for instance, in response to surgeon manipulation of one or both haptic input devices 110a,b at the master station 100.

FIG. 10C is a schematic illustration showing a representative translation unit 510 associated with or carried by the docking station 500, and a representative manner in which the collar elements 430a-c corresponding to the actuation assemblies 400a,b and the imaging endoscope assembly 450 are retained by corresponding translation unit clips 530a-c. The translation unit 510 can include an independently adjustable/displaceable translation stage corresponding to each actuation assembly 400a,b as well as the imaging endoscope assembly 450. In a representative implementation, a given translation stage can include or be a ball screw or a linear actuator configured for providing longitudinal/surge displacement to a corresponding clip 530 across a predetermined maximum distance range, in a manner readily understood by one having ordinary skill in the relevant art.

FIGS. 11A-11C illustrate a docking mechanism by which the transport endoscope 300 can be matingly engaged with docking station 500 in accordance with an embodiment of the present disclosure. Referring to FIG. 11A-11C, a joint member 540 is formed on a surface of docking station 500. The joint member 540 comprises a protrusion 541, a plurality of bumps 542 formed on side surfaces of the protrusion 541 and a locking lever 543. As shown in FIG. 11A, an endoscopist aligns and engages the transport endoscope's main body 310 with the joint member 540 in a direction indicated by arrow 551a. And then, as shown in FIG. 11B, when the endoscopist rotates the locking lever 543 in the direction of arrow 551b, the transport endoscope's main body 310 is docked with the joint member 540 of docking station. Also, the endoscopist can release the transport endoscope 300 by rotating the locking lever 543 in the direction of arrow 551c and disengaging the transport endoscope 300 in the direction of arrow 551d.

Figure 12:
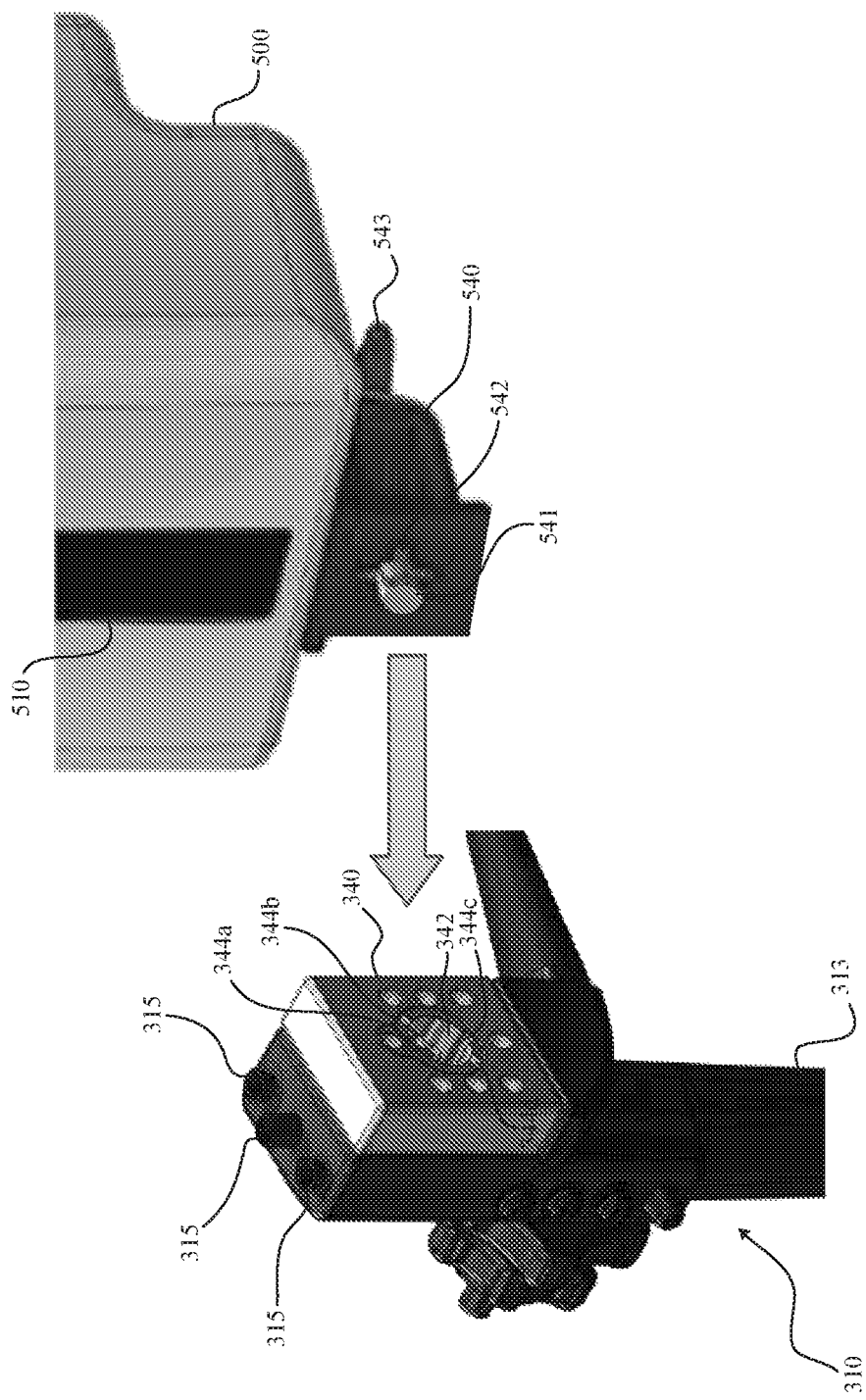
FIG. 12 illustrates a docking mechanism of FIGS. 11A-11C in more details.

FIG. 12 shows the docking mechanism of FIGS. 11A-11C in more detail. As shown in FIG. 12, a joint member 340 of transport endoscope may comprise a groove 342 for accommodating the docking station's joint member 540 and slots 344a-344d which are matingly engaged with bumps 542 of joint member of docking station 500. In the embodiment described referring to FIGS. 11A-12 or FIG. 10A, the transport endoscope 300 is engageable with the docking station 500 from the same direction as the direction from which the at least one of flexible elongate is matingly engaged with the translation unit 510.

Figure 13C:
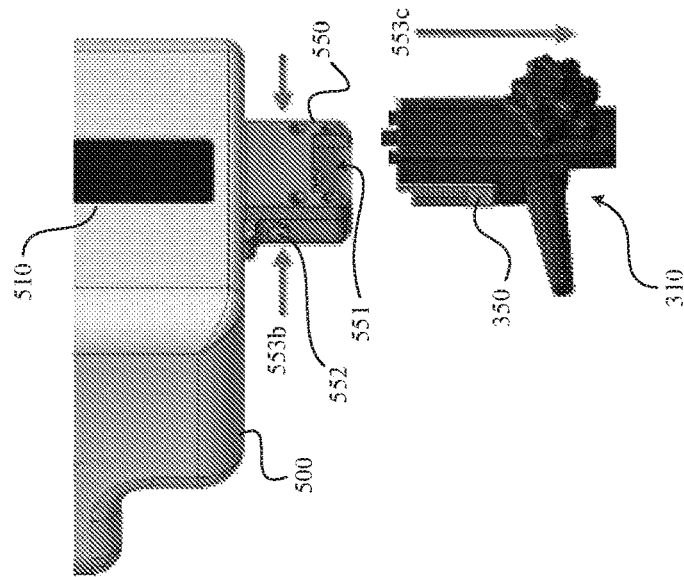
FIGS. 13A-13C illustrate a docking mechanism by which the transport endoscope can be matingly engaged with docking station in accordance with another embodiment of the present disclosure.
Figure 13B:
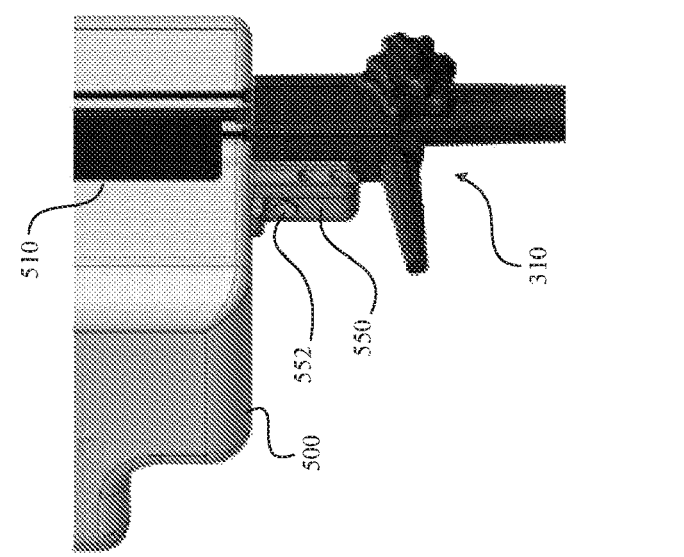
Figure 13A:
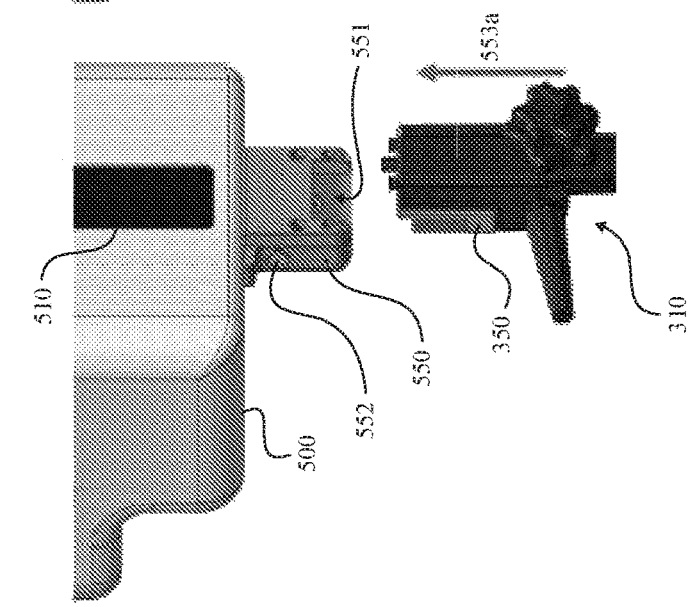

FIGS. 13A-13C illustrate a docking mechanism by which the transport endoscope 300 can be matingly engaged with docking station 500 in accordance with another embodiment of the present disclosure. Referring to FIG. 13A-13C, a joint member 550 of docking station 500 may comprise a slot 551 where the main body 310 of transport endoscope may be inserted and a pair of release buttons 552 which, when pushed, releases the engagement of the joint member 550 and the main body 310 of the transport endoscope. As shown in FIG. 13A-13B, an endoscopist may align and engage the main body 310 with the joint member 550 of the docking station by sliding the main body 310 into the slot 551 in a direction of arrow 553a. When a set of release buttons 552 is activated in a direction of the depicted arrow 553b, the main body 310 may be released from the docking station 500, in a manner readily understood by one having ordinary skill in the relevant art.

Figure 14:
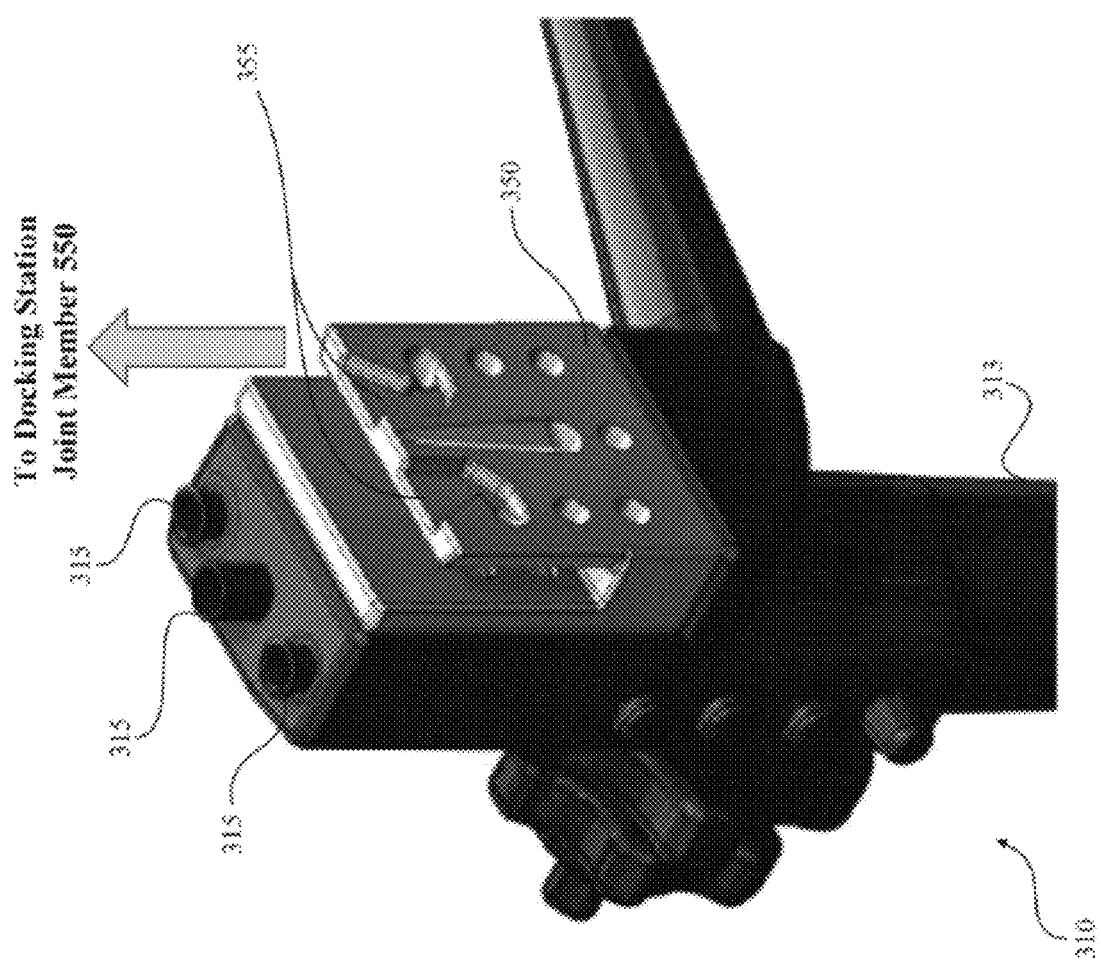
FIG. 14 shows an illustration of transport endoscope's main body 310 for docking mechanism of FIGS. 13A-13C in accordance with an embodiment of the present disclosure.

FIG. 14 shows an illustration of transport endoscope's main body 310 for the docking mechanism of FIGS. 13A-13C in accordance with an embodiment of the present disclosure. As shown FIG. 14, the joint member 350 of transport endoscope's main body 310 may comprise clamping member 355 which may accommodate a counterpart inside slot 551 of joint member 550 in docking station 500 (not shown). In the embodiment described referring to FIGS. 13A-14, the transport endoscope is engageable with the docking station from a direction parallel to the central axis of the flexible elongate shaft 320, e.g., at the flexible elongate shaft's proximal end 321a.

Figure 15:
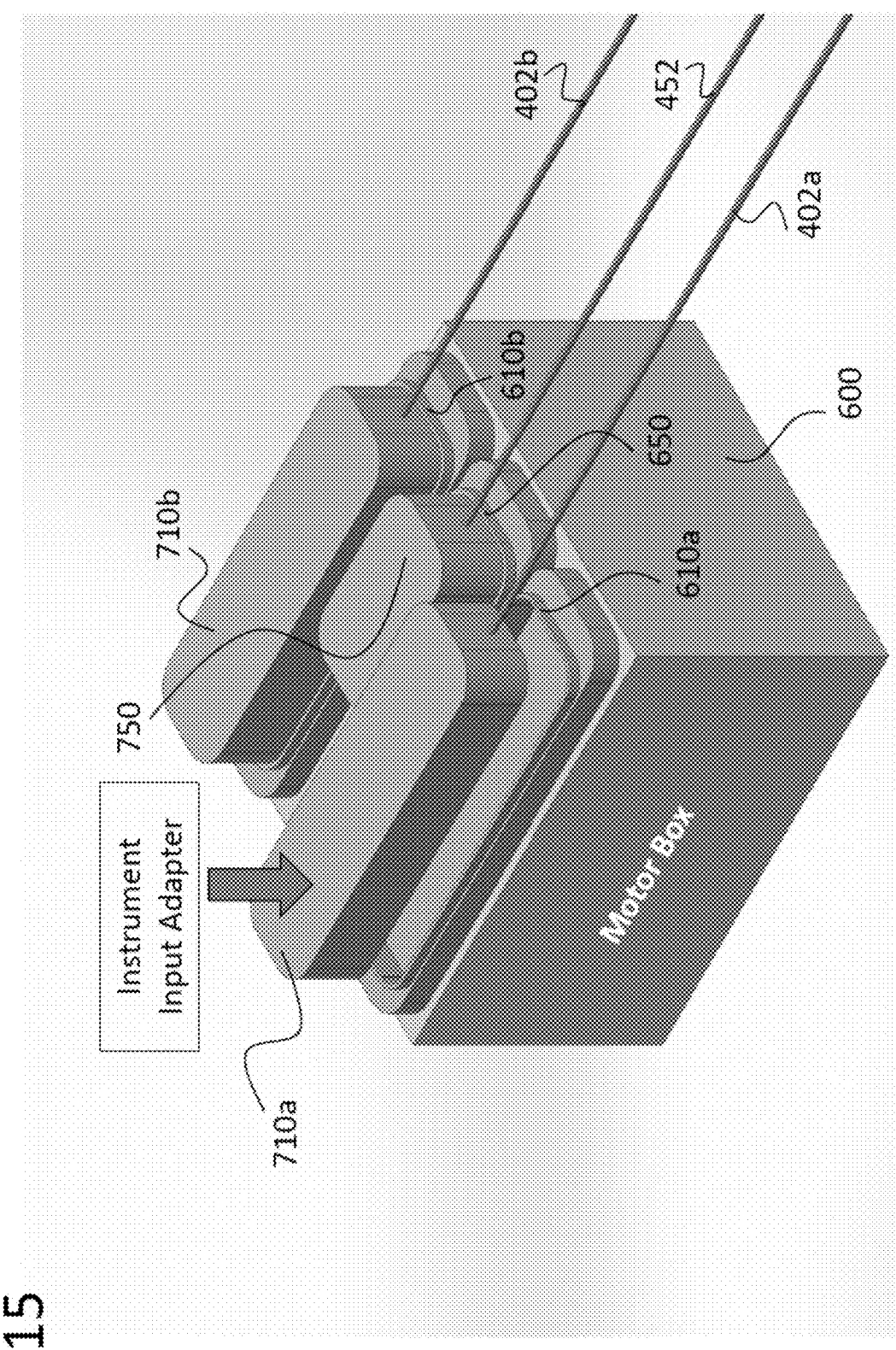
FIG. 15 is a schematic illustration showing coupling of an instrument input adapter of each actuation assembly to a corresponding instrument output adapter corresponding to a motorbox in accordance with an embodiment of the present disclosure.

FIG. 15 is a schematic illustration showing coupling of each actuation assembly's instrument input adapter 710a,b to a corresponding instrument output adapter 610a,b of the motorbox 600 in accordance with an embodiment of the present disclosure. By way of such adapter-to-adapter coupling, tendons internal to each actuation assembly's outer sleeve/coil 402a,b can be mechanically coupled or linked to particular actuators or motors within the motorbox 600. For any given actuation assembly 400, such tendons are configured for positioning or maneuvering the robot arm 410a,b and corresponding end effector 420a,b in accordance with predetermined DOFs, for instance, in a manner indicated in (a) International Patent Application No. PCT/SG2013/000408; and/or (b) International Patent Publication No. WO 2010/138083. Consequently, each actuation assembly's robot arm 410a,b and end effector 402a,b can be selectively positioned or manipulated relative to the distal end 321b of the flexible elongate shaft 320 as a result of the selective application of tension to the tendons within the actuation assembly 400a,b by way of one or more actuators/motors within the motorbox 600 that are associated with robot arm/end effector position control. Moreover, such adapter-to-adapter coupling enables the establishment, re-establishment, or verification of intended, desired, or predetermined tension levels in the tendons within each actuation assembly 400a,b prior to the initiation of an endoscopic procedure (e.g., tendon pretension levels), and in some embodiments on-the-fly establishment or adjustment of tendon tension levels during an endoscopic procedure. Furthermore, in various embodiments, such adapter-to-adapter coupling enables the maintenance of a given or predetermined tension level (e.g., a predetermined minimum tension level) in actuator assembly tendons when the instrument input adapter 710a,b is not engaged with, or disengaged from, the instrument output adapter 610a,b, as further detailed hereafter.

Representative Input Adapter and Output Adapter Structures and Couplings

Figure 16:
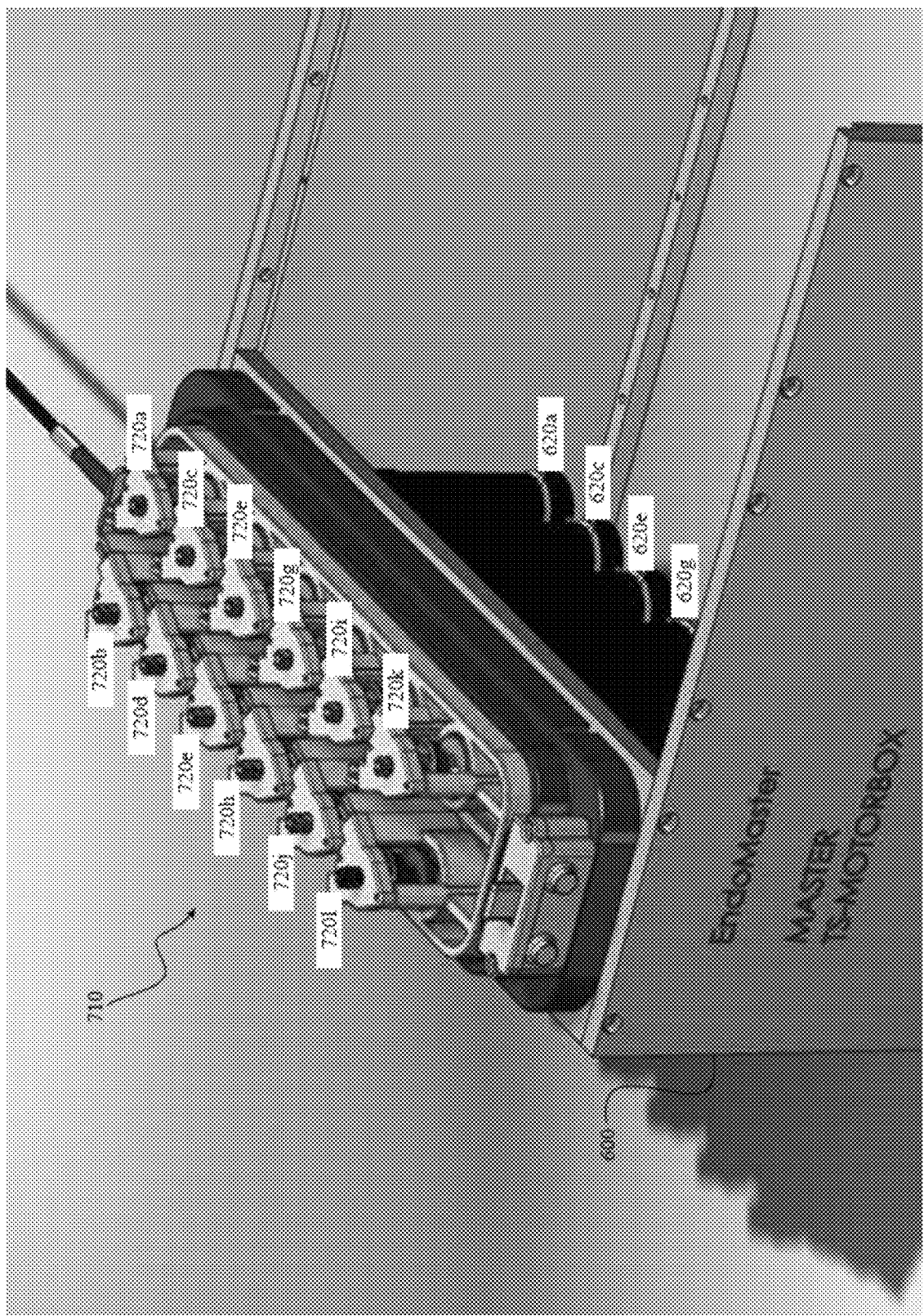
FIG. 16 is a perspective cutaway view showing representative internal portions of an instrument input adapter mounted to an instrument output adapter of the motorbox in accordance with an embodiment of the present disclosure.
Figure 17:
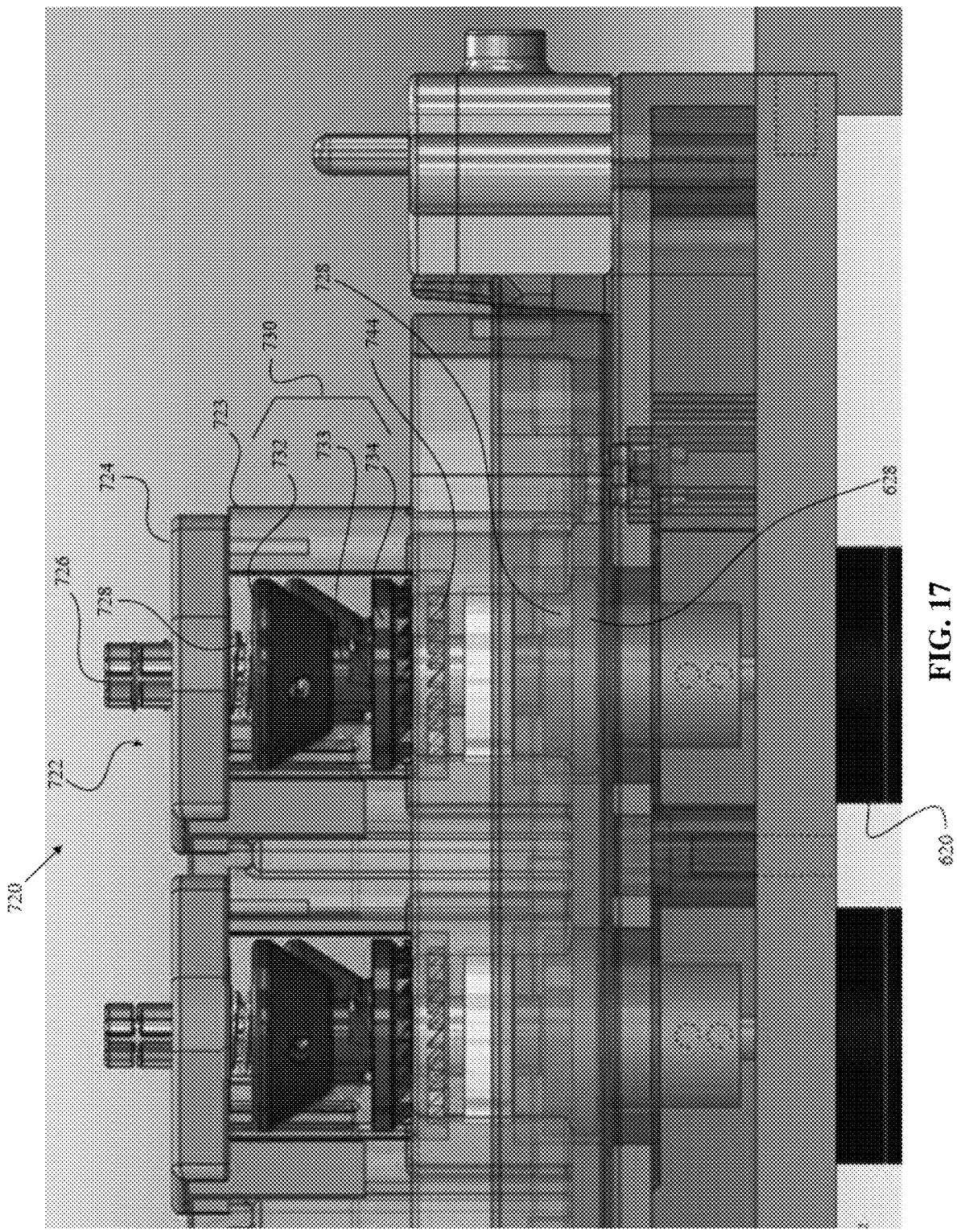
FIG. 17 is a corresponding cross sectional illustration showing representative internal portions of the instrument adapter and instrument output adapter when coupled together or matingly engaged in accordance with an embodiment of the present disclosure.

FIG. 16 is a perspective cutaway view showing representative internal portions of an actuation assembly's instrument input adapter 710 mounted to an instrument output adapter 610 of the motorbox 600 in accordance with an embodiment of the present disclosure. FIG. 17 is a corresponding cross sectional illustration showing representative internal portions of the instrument adapter 710 and instrument output adapter 610 when coupled together or matingly engaged in accordance with an embodiment of the present disclosure. FIGS. 18A-18D are cross sectional illustrations showing representative internal portions of actuation engagement structures 720 provided by the instrument input adapter 710, and the positions of elements therein, corresponding to various phases of engagement of the instrument input adapter 710 with and disengagement of the instrument input adapter 710 from the instrument output adapter 610 in accordance with an embodiment of the present disclosure.

With reference to FIG. 16, in an embodiment the instrument input adapter 710 includes a plurality of actuation engagement structures 720, such as an individual actuation engagement structure 720 for each motorbox actuator/motor 620 that is configured for controlling the robot arm/end effector 410, 412 of the particular actuation assembly 400 with which the instrument input adapter 710 is associated.

In certain embodiments, the motorbox 600 includes a single actuator/motor for controlling each DOF of the robot arm/end effector 410, 412, in which case the instrument input adapter 710 includes a single actuation engagement structure 720 corresponding to each such DOF. In such embodiments, any given DOF corresponds to a single tendon (which resides within its particular sheath).

In various embodiments, the motorbox 600 includes dual or paired actuators/motors 620 for controlling each DOF provided by the actuation assembly's robot arm/end effector 410, 412. In such embodiments, any given DOF corresponds to a pair of tendons (e.g., a first tendon that resides within a first sheath, and a second tendon that resides within a second sheath). In this case, two actuators/motors within the motorbox 600 are actuated synchronously relative to each other such that a given pair of tendons (e.g., the first tendon and the second tendon) control a given DOF of the robot arm/end effector 410, 412.

As a result, the instrument input adapter 710 correspondingly includes a pair of actuation engagement structures 720 corresponding to each robot arm/end effector DOF. In a representative implementation in which a robot arm/end effector 410, 412 are positionable/manipulable with respect to six DOFs, the motorbox 600 includes twelve actuators/motors 600a-1 for controlling this robot arm/end effector 410, 412, and the instrument input adapter 710 includes twelve actuation engagement structures 720a-1. The instrument input adapter 710 mounts to the motorbox 600 such that a particular pair of actuation engagement structures 720 (e.g., actuation engagement structures 720 disposed in a side-by-side manner relative to each other along a length of the instrument input adapter 710) corresponds to and is mechanically coupled to a counterpart pair of actuators/motors 620a-1 within the motorbox 600 for providing robot arm/end effector manipulability/positionability with respect to a particular robot arm/end effector DOF.

As indicated in FIG. 17 and also FIGS. 18A-18D, in an embodiment an actuation engagement structure 720 includes (a) a frame member 722 having a plurality of arm members 723 that support a frame member platform 724 that defines an upper boundary of the frame member 722, where the frame member platform 724 is perpendicular or transverse to such arm members 723; (b) an elongate input shaft 726 that extends upwardly through a center or central region of the frame member's platform 724, and downwardly toward an output disk 626 of the motorbox output adapter 610 such that it can be engaged thereby, and which is displaceable along a longitudinal axis (e.g., in a vertical direction parallel to its length); (c) a drum structure 730 mounted to and circumferentially disposed around the input shaft 726, which includes (i) a tapered drum 732 having an upper surface, an outer surface, and a bottom surface, and (ii) a first ratchet element 734 carried perpendicular or transverse to the input shaft 726 at a predetermined distance away from the bottom surface of the drum 732; (d) a resilient biasing element or spring 728 circumferentially disposed around the input shaft 726, between an underside of the frame member's platform 724 and the upper surface of the drum 732; and (e) a second ratchet element 744 perpendicular or transverse to and circumferentially disposed around the input shaft 726, and disposed below the first ratchet element 734 at a predetermined distance away from the underside of the frame member's platform 724. In various embodiments, the second ratchet element 744 is positionally fixed, immovable, or non-displaceable relative to the input shaft 726.

The drum structure includes a collar portion 733 that defines a spatial gap between the bottom surface of the drum 732 and an upper surface of the first ratchet element 734. A proximal end of a tendon can be coupled, linked, or secured to a portion of the drum structure 730 (e.g., a crimp fixture/abutment carried on an upper surface of the first ratchet element 734), and the tendon can be tightly wound around the circumference of the drum structure's collar portion 733, such that the collar portion 733 carries multiple or many tendon windings thereabout. In a direction toward its opposite/distal end, the tendon wound about the collar portion 722 can extend away from the drum structure 730, toward, into, and along the length of the actuator assembly's outer sleeve/coil 402, until reaching a given location on the actuator assembly's robotic arm 410 (e.g., at a particular position relative to a robotic arm joint or joint element) or end effector 420.

Rotation of the drum structure 730, or correspondingly rotation of the input shaft 726, results in further winding of the tendon about the drum structure's collar portion 733, or partial unwinding of the tendon from the collar portion 733, depending upon the direction in which the drum structure 730 is rotated. Winding of the tendon about the collar portion 733 results in an increase in tendon tension, and can reduce the length of the tendon that resides within the actuator assembly's outer sleeve/coil 402; and unwinding the tendon from the collar portion 733 results in a decrease in tendon tension, and can increase the length of the tendon that resides within the actuation assembly's outer sleeve/coil 402, in a manner readily understood by one having ordinary skill in the relevant art. Consequently, selective tendon winding/unwinding facilitates or enables the precise manipulation/positioning of the robotic arm/end effector 410, 412 relative to a particular DOF.

More particularly, in an embodiment providing dual motor control for each DOF, synchronous winding/unwinding of paired tendons corresponding to a specific DOF, by way of synchronous rotation of counterpart drum structures 730, results in the manipulation/positioning of the robotic arm/end effector 410, 412 in accordance with this DOF. Such synchronous drum structure rotation can selectively/selectably occur by way of a pair of actuator/motors 620 and corresponding output disks 626 to which actuation engagement structure input shafts 726 can be rotationally coupled, as further detailed below.

Figure 18A:
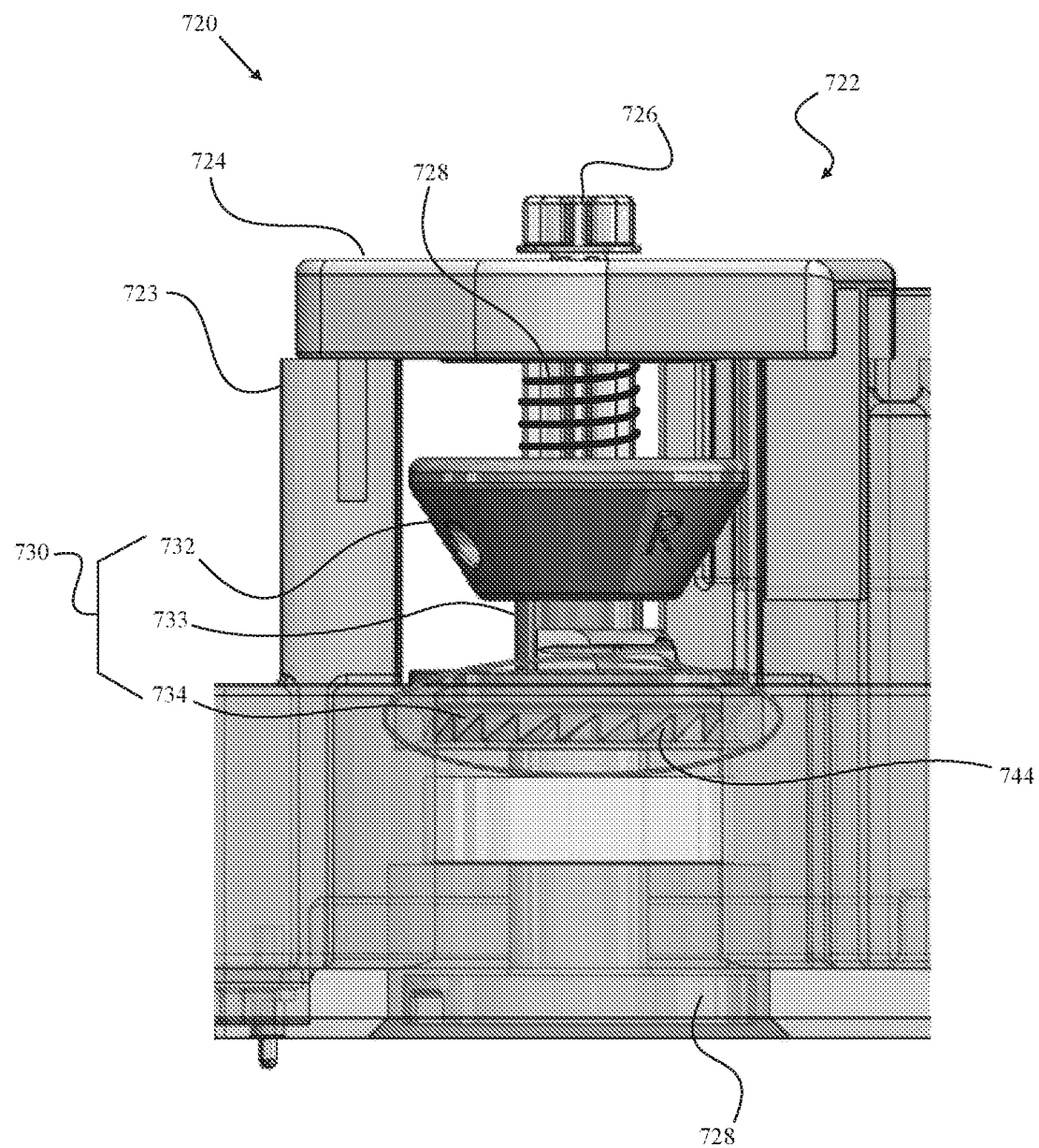
FIGS. 18A-18D are cross sectional illustrations showing representative internal portions of actuation engagement structures of the instrument input adapter, and the positions of elements therein, corresponding to particular phases of engagement of the instrument input adapter with and disengagement of the instrument input adapter from the instrument output adapter in accordance with an embodiment of the present disclosure.

When the instrument input adapter 710 is not engaged with or has been disengaged from the instrument output adapter 610 of the motorbox 600, an actuation engagement structure's spring 728 biases or pushes the actuation engagement structure's drum structure 730 downward to a first or default position, such that the first ratchet element 734 securely matingly engages with the second ratchet element 744. Such engagement of the first ratchet element 734 with the second ratchet element 744 when the spring 728 biases the drum structure downward 730 is illustrated in FIG. 18A. As a result of such engagement of the first and second ratchet elements 734, 744, the drum structure 730 is prevented from rotating, and thus the tension in the tendon corresponding to the drum structure 730 is maintained or preserved (e.g., the tension in the tendon cannot change or appreciably change).

Figure 18B:
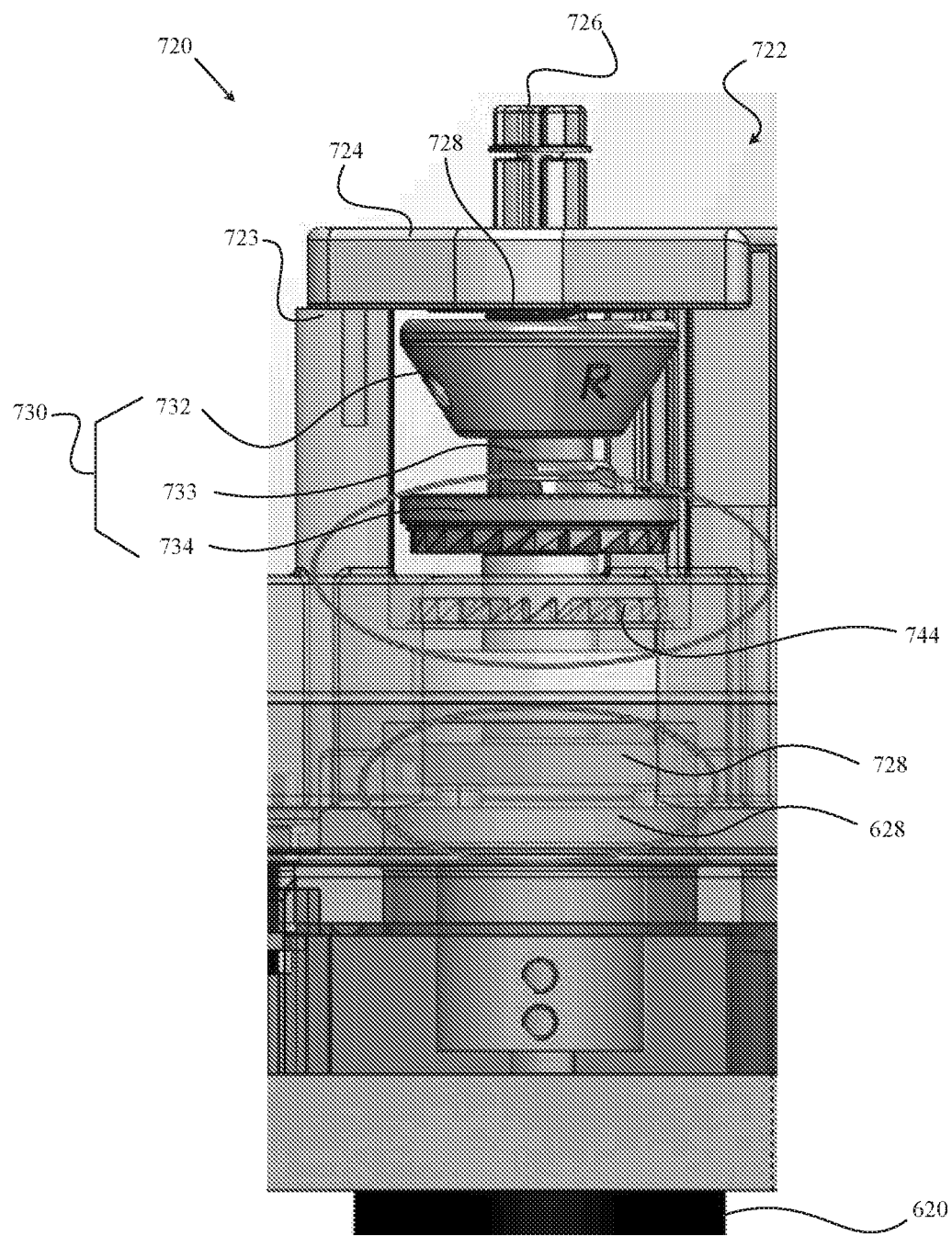

As indicated above, the actuation engagement structure's input shaft 726 is displaceable parallel to or along its longitudinal axis. As the instrument input adapter 710 is mounted or installed onto the instrument output adapter 610 of the motorbox 600 (e.g., by way of one or more snap-fit couplings), a bottom surface of a lower plate 728 carried by the input shaft 726 below the second ratchet element 744 contacts a set of projections carried by an upper surface of an output disk 628 associated with a particular actuator/motor 620. Consequently, the spring 728 is compressed, and the input shaft 726 and the drum structure 730 carried thereby are upwardly displaced such that the distance between the upper surface of the drum 732 and the underside of the frame member's platform 724 decreases, as indicated in FIG. 18B. Such upward displacement of the drum structure 730 causes the first ratchet element 734 to disengage from the second ratchet element 744. This can correspond to a situation in which the instrument input adapter 710 is installed or mounted on the instrument output adapter of the motorbox 600, but the input shaft 726 is not yet rotationally rotatably/rotationally coupled to with the output disk 626 of the actuator/motor 620.

During the mounting of the instrument input adapter 710 onto the instrument output adapter 610 of the motorbox 600, or once the instrument input adapter 710 is fully/securely mounted onto the instrument output adapter 610 (e.g., as can be detected by way of a set of sensors), corresponding to a situation in which the input shaft 726 and drum structure 730 have been vertically displaced upward and the first and second ratchet elements have become disengaged from each other, the actuators/motors 620 within the motorbox 600 commence an initialization process (e.g., under the direction of the control unit 800). During the initialization process, each actuator/motor 620 rotates its corresponding output disk 628 until the set of projections carried by the output disk 628 catch or matingly engage with counterpart recesses within the bottom surface of the input shaft's lower plate 728.

Figure 18C:
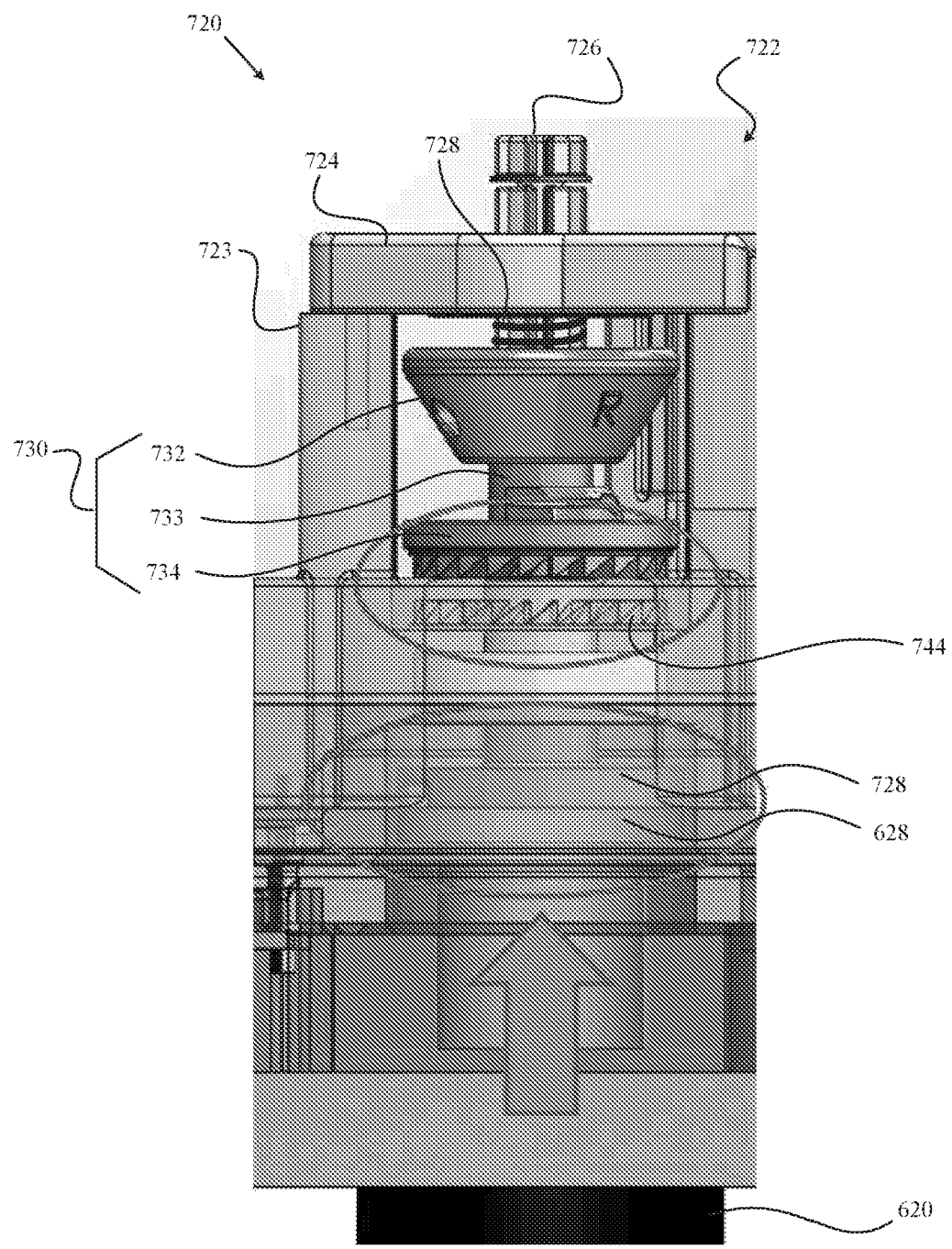

Once the projections carried by the output disk 628 catch or matingly engage with counterpart recesses formed in the input shaft's lower plate 728, the input shaft 726 is rotationally coupled to an intended actuator/motor 620, in a manner illustrated in FIG. 18C. When such output disk projections and lower plate recesses are rotationally coupled, the actuator/motor 620 can selectively precisely control the winding and unwinding of the tendon about the collar portion 733 of the drum structure 730, and/or precisely control tendon tension, to thereby manipulate/position the robotic arm/end effector 410, 412 in an intended manner in response to surgeon input received at the master station 100.

Figure 18D:
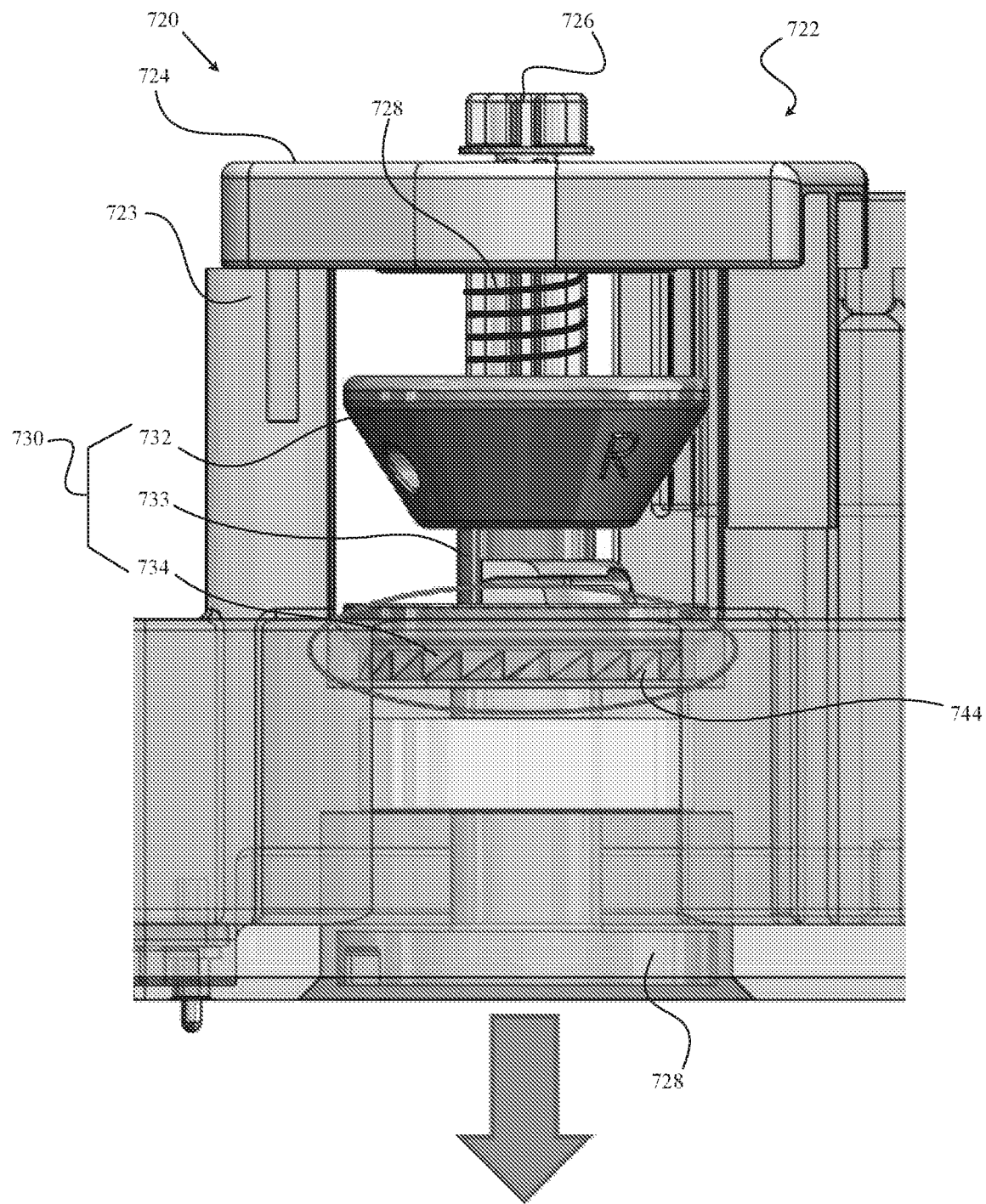

When the instrument input adapter 710 is disengaged, dismounted, or detached from the instrument output adapter 610, decompression of the spring 728 pushes the upper surface of the drum structure 730 downward, such that the first ratchet element 734 matingly engages with the second ratchet element 744 in a manner illustrated in FIG. 18D.

Rotation of the input shaft 726 and the disc structure 730 are then prevented, and tendon tension is thus maintained in a manner essentially identical or analogous to that described above in relation to FIG. 18A.

Aspects of particular embodiments of the present disclosure address at least one aspect, problem, limitation, and/or disadvantage associated with exiting master-slave flexible robotic endoscopy systems and devices. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

We claim:

1. A robotic endoscopy system, comprising:
   at least one flexible elongate assembly configured to perform endoscopic procedures according to forces generated by external actuation elements;

a transport endoscope having a main body and a flexible elongate shaft comprising a central axis and a plurality of channels therewithin for carrying portions of the at least one flexible elongate assembly;

a transport endoscope housing, wherein the transport endoscope housing comprises the main body at a proximal end of the transport endoscope housing, the main body comprising a top surface perpendicular to the central axis of the flexible elongate shaft at the proximal end of the transport endoscope and a plurality of side surfaces, and wherein one or more insertion inlets are located on the top surface of the main body and a joint member is located on one of the plurality of side surfaces, and wherein each of the one or more insertion inlets have an insertion axis which is parallel to the central axis of the elongate shaft at the proximal end of the transport endoscope, and wherein access to the plurality of channels within the elongate shaft at the proximal end of the transport endoscope for the at least one flexible elongate assembly is only via the one or more insertion inlets;

a docking station configured to be detachably engaged with the proximal end of the transport endoscope by the docking station engaging with the joint member on the transport endoscope housing, the docking station having a translation unit configured to matingly engage with the at least one flexible elongate assembly and selectively longitudinally translate the at least one flexible elongate assembly across a predetermined distance range;

a motorbox comprising a plurality of actuators, each of the plurality of actuators configured to be mechanically coupled to and drive each of the at least one flexible elongate assembly; and a main control unit communicatively coupled to the motorbox and configured to control each of the plurality of actuators according to one or more external control signals, wherein the transport endoscope is engageable with the docking station from one of: (a) the same direction as the direction from which the at least one flexible elongate assembly is matingly engaged with the translation unit, and (b) a direction parallel to the central axis of the flexible elongate shaft.

2. The robotic endoscopy system of claim 1, further comprising, a support function connector assembly configured to couple the main body of the transport endoscope housing to an external system for supporting functions including at least one of delivery of insufflation, positive pressure, suction, negative pressure, vacuum pressure, and irrigation through the flexible elongate shaft of the transport endoscope.

3. The endoscopy system of claim 1, wherein the motorbox comprises at least one adapter, each of the at least one adapter of the motorbox communicatively coupled to the external actuation elements.

4. The endoscopy system of claim 1, wherein each of the at least one flexible elongate assembly further comprises a collar element configured to surround at least a portion of an outer sleeve of the flexible elongate assembly at a predetermined distance away from a distal end of the flexible elongate assembly and configured to enable longitudinal translation of the flexible elongate assembly across a predetermined distance range.

5. The endoscopy system of claim 4, wherein the translation unit comprises at least one collar receiver configured to be matingly engaged with the collar element and having means for enabling the longitudinal translation.

6. The endoscopy system of claim 1, wherein one of the at least one flexible elongate assembly comprises a flexible imaging endoscope assembly, the flexible imaging endoscope assembly comprising:

an imaging unit configured to capture images of one or more end effectors coupled to respective one or more distal ends of the at least one flexible elongate assembly;

a plurality of tendon elements configured for spatially positioning the imaging unit in response to applied forces; and an adapter by which the plurality of tendon elements can be interfaced with particular ones of the external actuation elements.

* * * * *